(12) United States Patent
Bacque et al.

(10) Patent No.: US 6,194,426 B1
(45) Date of Patent: *Feb. 27, 2001

(54) 5,6,7,8 TETRAHYDROINDOLIZINES DERIVATIVES

(75) Inventors: Eric Bacque, Morsang sur Orge; Conception Nemecek; Georges Bashiardes, both of Thiais; Norbert Dereu, Viry-Chatillon, all of (FR)

(73) Assignee: Rhona-Poulenc Rorer S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/981,095

(22) PCT Filed: Jun. 12, 1996

(86) PCT No.: PCT/FR96/00887

§ 371 Date: Dec. 12, 1997

§ 102(e) Date: Dec. 12, 1997

(87) PCT Pub. No.: WO97/00073

PCT Pub. Date: Jan. 3, 1997

(30) Foreign Application Priority Data

Jun. 14, 1995 (FR) .................................................. 95 07055

(51) Int. Cl.[7] ........................ A61K 31/437; C07D 221/00
(52) U.S. Cl. ........................ 514/299; 514/226.8; 514/338; 546/112; 546/270.1; 544/47
(58) Field of Search ............................... 546/112; 514/299

(56) References Cited

U.S. PATENT DOCUMENTS

| | | | |
|---|---|---|---|
| 4,063,928 | * 12/1977 | Johnston | 546/290 |
| 4,584,297 | * 4/1986 | Fabre et al. | 546/112 |
| 4,684,658 | 8/1987 | Fabre et al. | 546/112 |
| 5,071,859 | * 12/1991 | Kundsen et al. | 514/326 |

FOREIGN PATENT DOCUMENTS 0522944 1/1993 (EP).

OTHER PUBLICATIONS

Mitsuya et al. Nature vol. 325, pp. 7773778, Feb. 1987.*
English language Derwent Abstract of EP–A–0522944.
Fabre et al., Une Cycloaddition Dipolaire–1,3 Inattendue du Chloro–2 Acrylonitrile, Tetraheron Letters, 26(44):5447–5450 (1985).
Synthetic Organic Chemistry by Wagner et al. p.98, 1953.*
* cited by examiner Primary Examiner—Jane Fan
(74) Attorney, Agent, or Firm—Finnegan, Henderson, Farabow, Garrett & Dunner, L.L.P.

(57) ABSTRACT

A novel therapeutic use of pyrrole derivatives of the folloeing formula:

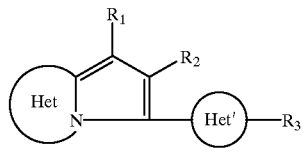

in which the variables are as defined in the specification and their salts thereof for treating conditions in which TNF is involved.

14 Claims, No Drawings

5,6,7,8 TETRAHYDROINDOLIZINES DERIVATIVES

This is a 371 of PCT/Fr96/00887 filed Jun. 12, 1996 now WO 97/00073 filed Jan. 3, 1997.

The present invention relates to a new therapeutic application of pyrrole derivatives of general formula:

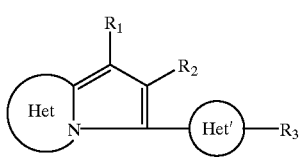

(I)

in which
Het denotes a ring condensed with pyrrole, such that it forms a pyrrolothiazole, 5,6,7,8-tetrahydroindolizine, dihydropyrrolothiazine or dihydropyrrolizine ring,
$R_1$ is a carboxamide, cyano, carboxyl, alkoxy carbonyl, acyl or imidazolylcarbonyl radical,
$R_2$ is a hydrogen or halogen atom or an alkyl, alkenyl, trihalomethyl or cyano radical,
$R_3$ is a hydrogen or halogen atom or a hydroxyl or alkyl radical, and
Het' is a pyridyl, pyridyl N-oxide or thiazolyl radical,
it being understood that the alkyl or acyl radicals are straight or branched and contain 1 to 4 carbon atoms and the alkenyl radicals are straight or branched and contain 2 to 4 carbon atoms, and of its salts when they exist.

It is also understood that when $R_2$ and/or $R_3$ are halogen, they may be chosen from chlorine, bromine, fluorine or iodine.

Pyrrole derivatives which have an antithrombotic activity or are used as intermediates for the preparation of antithrombotic derivatives have been described in European Applications EP 118 321, EP 147 317 and EP 124 384 and in French Application 2 539 417.

It has now been found that the derivatives of general formula (I) inhibit the effects of the TNF (Tumour Necrosis Factor) and can consequently find an application in all the fields where this mediator is involved. The present invention therefore relates to the application of the pyrrole derivatives of general formula (I) for the preparation of a medication intended for the treatment of the disorders in which the TNF is involved.

The TNF is responsible especially for the activation of the HIV virus especially in chronically infected cells.

Consequently, the products of general formula (I) can be useful for obtaining a medication intended for the prophylaxis and/or therapeutic treatment of retroviral infections and more particularly of AIDS (acquired immunodeficiency syndrome) and of associated syndromes [ARC (AIDS related complex)].

By prophylaxis we imply the treatment of individuals who have been exposed to the HIV viruses (human immunodeficiency viruses), in particular the asymptomatic seropositives who carry the risk of developing the disease in the months and years to come after the primary infection.

The activity of the products of general formula (I) has been revealed as follows:

The effects of the derivatives of general formula (I) on the induction of the HIV-1 virus have been studied on chronically infected cell lines.

U1 cell lines are employed, obtained after infection of the premonocyte line, U937, with the HIV-1 virus and selected according to the ability to increase virus production in response to phorbol myristate acetate (PMA), to the TNF and to other mediators [Folks et al., Science 238, 800 (1987)]. Reverse transcriptase activity is employed as an indicator of virus production. The effect of increasing concentrations of the product to be studied on stimulated cell lines is thus analysed.

Experimental Study

The product to be studied is dissolved in dimethylformamide (DMF). The parent solutions are prepared on the day of the test and stored at a temperature of 4° C. The dilutions are produced so that the DMF concentration remains constant (0.1%)

The cell cultures are sampled in an exponential growth phase and recultured at the rate of a final concentration of $2\times10^5$ cells/ml, in the presence of various concentrations of the product to be studied. αTNF or PMA is added to all the cultures 30 minutes later.

Each test is done in triplicate, including the controls. Three days later a fraction of supernatant of the cultures is sampled and frozen with a view to the measurement of reverse transcriptase.

The measurement of reverse transcriptase activity is carried out using known techniques, in duplicate [Strebel et al., Nature, 328, 728 (1987)].

The derivatives of general formula (I) are studied at concentrations of from 0.1 nM to 10 μM.

The αTNF is added at a rate of 10 Units/ml and PMA at $10^{-8}$ M (final concentration).

Some controls do not receive the activator. Other controls do not receive the product to be studied. Others receive neither the product nor the activator.

Results

The decrease in virus production by the derivatives of general formula (I) is significant and dose-dependent in the case of U1 cells treated with ATNF or with PMA. On day 3 a decrease of at least 50% is seen in the production of reverse transcriptase in the case of the U1 cells treated with 10 Units/ml of αTNF and to which products have been added in a concentration of 10 μM.

Furthermore, the derivatives of general formula (I) have no effect on the viability of the cells at the active concentrations.

By way of example, the results for some products appear in Table I below.

TABLE 1
| Example No. | Het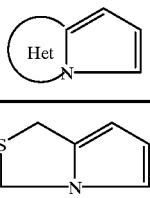 | R₁ | R₂ | Het'-R₃ | 50% inhibiting concentration (nM) | |
|---|---|---|---|---|---|---|
| | | | | | PMA | TNF |
| a | 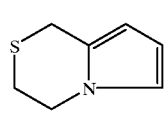 | CONH₂ | H | 3-Pyridyl | 1000 | 3000 |
| b | 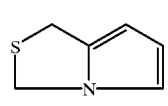 | CONH₂ | H | 3-Pyridyl | 300 | 700 |
| c | 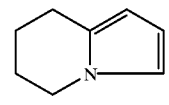 | CONH₂ | CH₃ | 3-Pyridyl | 100 | 240 |
| d | 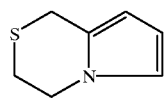 | CONH₂ | H | 3-Pyridyl | 1000 | 3000 |
| e | 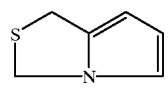 | CONH₂ | CH₃ | 3-Pyridyl | 230 | 110 |
| f | 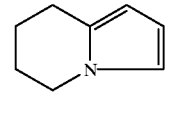 | CN | H | 3-Pyridyl | 1000 | 10000 |
| g | 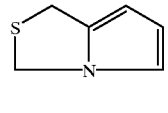 | CN | H | 3-Pyridyl | 1000 | 1000 |
| h | 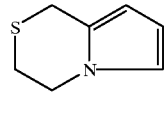 | COCH₃ | H | 3-Pyridyl | 300 | 1000 |
| i | 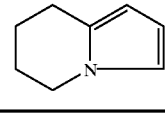 | CONH₂ | H | 3-Pyridyl | 390 | 1720 |
| j | 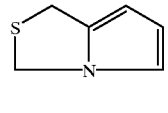 | COOH | H | 3-Pyridyl | 3000 | 1000 |

The preparation of the products of general formula (I) is performed according to the methods described in the above-mentioned patent applications, especially according to the methods described in European Application EP 147 317 or according to the examples which follow, or by analogy with these methods.

When $R_1$ is a carboxamide, cyano, carboxyl, acyl or alkoxycarbonyl or imidazolylcarbonyl radical, then an acrylic derivative of general formula:

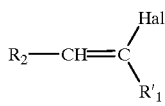

(II)

in which $R_2$ is defined as above and $R'_1$ is a cyano or acyl radical and Hal is a halogen atom, preferably a chlorine atom, is reacted with an acid of general formula:

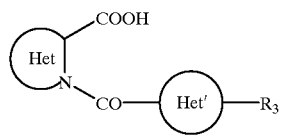

(III)

in which Het and Het'—$R_3$ are defined as above, and the product obtained is then optionally hydrolysed either to amide or to acid according to the known methods which do not alter the remainder of the molecule, and the acid obtained is then optionally converted into an ester to obtain a derivative in the case of which $R_1$ is alkoxycarbonyl, or the acid obtained is optionally converted into an imidazole derivative by the action of carbonyldiimidazole, to obtain a derivative by in the case of which $R_1$ is imidazolylcarbonyl, and then the pyridyl radical denoting Het' is optionally oxidized when the intention is to obtain a product in the case of which Het' denotes pyridyl N-oxide.

The reaction of the product of general formula (II) with the acid of general formula (III) is generally performed in acetic anhydride at a temperature of between 80 and 130° C.

The hydrolysis to amide is performed according to known methods, especially by heating in an alkaline medium in an organic solvent like, for example, t-butanol at a temperature of between 30 and 85° C., or in a concentrated acidic medium at a temperature of between 20 and 100° C.

The hydrolysis to acid is performed according to known methods, especially in a basic medium in an alcohol of high boiling point, for example in the presence of potassium hydroxide in ethylene glycol, at a temperature of between 100° C. and the reflux temperature of the reaction mixture.

The conversion of the acidic functional group to an alkoxycarbonyl radical is performed by the usual esterification methods which do not alter the remainder of the molecule.

The conversion of the acidic functional group to an imidazole radical is performed in a solvent like tetrahydrofuran at a temperature of between 20 and 40° C.

The oxidation of the pyridyl radical is performed by any oxidation method which does not alter the remainder of the molecule. The operation is carried out especially by means of a peracid like m-chlorobenzoic acid, in an alcoholic medium (for example ethanol).

Among the products of general formula (I) the products in the case of which a) Het, Het', $R_2$ and $R_3$ are defined as above and $R_1$ is alkoxycarbonyl, acyl containing 1, 3 or 4 carbon atoms) or imidazolylcarbonyl,
b) Het, Het', $R_1$ and $R_3$ are defined as above and $R_2$ is alkenyl, trihalomethyl or cyano,
c) Het, $R_1$, $R_2$ and $R_3$ are defined as above and Het' is 4-pyridyl or 2-pyridyl or else Het, $R_1$ and $R_2$ are defined as above, $R_3$ is halogen or hydroxyl and Het' is 3-pyridyl or 5-thiazolyl,
d) Het', $R_2$ and $R_3$ are defined as above, $R_1$ is a carboxyl or acetyl radical and Het condensed with the pyrrole nucleus denotes a 2,3-dihydro-1H-pyrrolizine ring, and their salts when these exist, are new products.

Among the products of general formula (I) the products in the case of which a) Het is defined as above, Het' is 3-pyridyl or 5-thiazolyl, $R_1$ is cyano, $R_2$ is hydrogen, halogen or alkyl and $R_3$ is hydrogen, or
b) Het', $R_2$ and $R_3$ are defined as above in a), $R_1$ is a carboxyl or acetyl radical and Het condensed with the pyrrole nucleus denotes a 1H, 3H-pyrrolo[1,2-c]thiazole, 5,6,7,8-tetrahydroindolizine or 1,2-dihydro-4H-pyrrolo[1,2-c]thiazine ring, and their salts, when these exist, are known products in the case of which no pharmaceutical activity had hitherto been found.

Among the products of general formula (I) the following products, in the case of which $R_1$ is carboxamide, cyano, carboxyl or acetyl and $R_3$ is hydrogen: 3-(4-pyridyl)-5,6,7,8-tetrahydroindolizine-1-carboxamide; 2-bromo-3-(4-pyridyl)-5,6,7,8-tetrahydroindolizine-1-carboxamide; 6-bromo-5-(3-pyridyl)-1H,3H-pyrrolo[1,2-c]thiazole-7-carbonitrile; 6-methyl-5-(5-thiazolyl)-1H,3H-pyrrolo[1,2-c]thiazole-7-carboxamide; 2-bromo-3-(3-pyridyl)-5,6,7,8-tetrahydroindolizine-1-carbonitrile; 2-bromo-3-(3-pyridyl)-5,6,7,8-tetrahydroindolizine-1-carboxamide; 2-iodo-3-(3-pyridyl)-5,6,7,8-tetrahydroindolizine-1-carboxamide; 2-methyl-3-(3-pyridyl)-5,6,7,8-tetrahydroindolizine-1-carbonitrile; 2-methyl-3-(3-pyridyl)-5,6,7,8-tetrahydroindolizine-1-carboxamide; 2-ethyl-3-(3-pyridyl)-5,6,7,8-tetrahydroindolizine-1-carbonitrile; 2-chloro-3-(3-pyridyl)-5,6,7,8-tetrahydroindolizine-1-carboxamide; 6-methyl-5-(3-pyridyl)-1H,3H-pyrrolo[1,2-c]thiazole-7-carboxylic acid; 3-(5-thiazolyl)-5,6,7,8-tetrahydroindolizine-7-carbonitrile; 2-methyl-3-(3-pyridyl)-5,6,7,8-tetrahydroindolizine-1-carboxylic acid; 2-chloro-3-(3-pyridyl)-5,6,7,8-tetrahydroindolizine-1-carboxylic acid; 2-bromo-3-(3-pyridyl)-5,6,7,8-tetrahydroindolizine-1-carboxylic acid; 6-chloro-5-(3-pyridyl)-2,3-dihydropyrrolizine-7-carboxamide; 1-acetyl-3-(3-pyridyl)-5,6,7,8-tetrahydroindolizine and 1-acetyl-2-bromo-3-(3-pyridyl)-5,6,7,8-tetrahydroindolizine have never been described previously.

It is understood that the present invention also relates to the pharmaceutical compositions including a product of general formula (I) or the preparation of these compositions. In these compositions the product of general formula (I), optionally in salt form, is in the pure state or in a form of association with one or more diluents or adjuvants which are compatible and pharmaceutically acceptable.

The pharmaceutical compositions according to the invention are especially capable of inhibiting the replication of retroviruses and therefore of reducing the progression towards the disease or of decreasing its severity in the infected individuals.

In particular, in the case of infections with HIV, by inhibiting the replication of this virus, they are capable of reducing the progression towards AIDS or of decreasing its severity in the infected individuals.

The pharmaceutical compositions according to the invention are capable of preventing or of slowing down the evolution of the individuals infected by retroviruses towards a more severe stage of the disease.

They can be employed by way of prevention or cure. "Prevention" is intended to mean the fact of preventing the evolution in individuals presenting an immunodeficiency and/or infected by retroviruses.

The constitution of these compositions will, of course, be adapted to the individual case of the digestive tract of the immunodepressed subjects.

The compositions can be employed orally, parenterally or rectally.

Sterile compositions for parenteral administration may be preferably aqueous or nonaqueous solutions, suspensions or emulsions. The solvent or carrier employed may be water, propylene glycol, a polyethylene glycol, vegetable oils, in particular olive oil, injectable organic esters, for example ethyl oleate, or other suitable organic solvents. These compositions may also contain adjuvants, in particular wetting, isotonizing, emulsifying, dispersing and stabilizing agents. The sterilization may be carried out in a number of ways, for example by asepticizing filtration, by incorporating sterilizing agents into the composition, by irradiation or by heating. They can also be prepared in the form of sterile solid compositions which may be dissolved at the time of use in an injectable sterile medium.

Tablets, pills, powders or granulates may be employed as solid compositions for oral administration. In these compositions the active product according to the invention (optionally associated with another pharmaceutically compatible product) is mixed with one or several inert diluents or adjuvants such as sucrose, lactose or starch. These compositions may also include substances other than diluents, for example a lubricant such as magnesium stearate.

Pharmaceutically acceptably emulsions, solutions, suspensions, syrups and elixirs containing inert diluents such as water or liquid paraffin may be employed as liquid compositions for oral administration. These compositions may also include substances other than diluents, for example wetting, sweetening or flavouring products.

The compositions for rectal administration are suppositories or rectal capsules which, besides the active principle, contain excipients such as cocoa butter, semisynthetic glycerides or polyethylene glycols.

In general, the medical practitioner will determine the posology which he or she considers the most appropriate as a function of the age, weight and factors pertaining to the product and to the individual to be treated. In adults the doses are generally between 25 and 1000 mg per day.

The following example, given without any limitation being implied, illustrates a composition according to the invention.

EXAMPLE

2-Chloro-3-(3-pyridyl)-5,6,7,8-tetrahydro-indolizine-1-carboxamide . . . 25 mg

Magnesium stearate: 1% . . . 2 mg

Acdisol: 1% . . . 2 mg

Colloidal silica: 0.5% . . . 1 mg

Lactose . . . 170 mg

The present invention also relates to the associations consisting of one or more derivatives of general formula (I) and/or, if appropriate, their salts, and of another active principle known for its antiretrovirus activity, optionally in the presence of pharmaceutically acceptable excipients.

The antiretrovirus agents which can be associated are chosen from agents which are compatible and inert with regard to the derivative of general formula (I). Without any limitation being implied, these agents are chosen from inhibitors of reverse transcriptase zidovudine (AZT), didanosine (DDI), dideoxycytidine (DDC), lamivudine (3TC), TIBO, nevirapine, PMEA etc.), from protease inhibitors like, for example, Saquinavir, ABT-538, MK 639 etc.), or from tat and rev protein inhibitors.

Furthermore, the anti-TNF activity is particularly advantageous since it permits an application to the treatment of the diseases in the mechanism of which this factor is also involved. Examples which may be mentioned are especially: disorders of the central and peripheral nervous system, cerebral and spinal traumas, cerebral ischaemia, Alzheimer's disease, Huntington's disease, Parkinson's disease, sclerosis in plaque form, tardive dyskinesia, septic shock, respiratory distress syndrome, asthma and other chronic respiratory diseases including infections with mycobacteria, bony resorption diseases, the reactions of a graft against the host, the allograft rejection, fever and myalgia related to infections, Crohn's disease, ulcerating colitis, malaria and the cerebral forms of malaria and cachexia.

The following examples illustrate the preparation of the products according to the invention or employed according to the invention.

Example 1

3.75 g of 2-chlorocrotononitrile are added to a solution of 5.16 g of para-toluenesulphonyl chloride in 120 cm$^3$ of 1,2-dichloroethane. The solution obtained is clear. 4 g of the sodium salt of N-(2-chloronicotinoyl)piperidine-2-carboxylic acid are added with stirring. The addition causes a rise in temperature from 20° C. to 28° C. and the mixture is kept stirred for one hour at ambient temperature. 3.8 cm$^3$ of triethylamine are then added dropwise and the temperature increases to 35° C. The solution is heated to 40° C. for one hour and 30 minutes. After cooling, the reaction mixture is concentrated at reduced pressure (2.7 kPa) at a temperature close to 60° C. A mixture of products is thus obtained which is chromatographed on a column of 1.8 cm diameter containing 90 g of silica (0.04–0.0063). Elution is carried out with chloroform at a pressure of 1.5 bar, 20-cm$^3$ fractions being collected. The homogeneous fractions are combined and concentrated at reduced pressure (2.7 kPa) at a temperature close to 60° C. 2.81 g of 2-methyl-3-(2-chloro-3-pyridyl)-5,6,7,8-tetrahydroindolizine-1-carbonitrile are thus obtained in the form of cream crystals melting at about 134° C.

The sodium salt of N-(2-chloronicotinoyl)piperidine-2-carboxylic acid can be prepared as follows:

A solution of 27.6 g of ethyl N-(2-chloronicotinoyl) piperidine-2-carboxylate in a mixture of 276 cm$^3$ of acetonitrile and 27 of ethanol is stirred at a temperature close to 20° C. An aqueous solution of sodium hydroxide is prepared from 3.72 g of sodium hydroxide pellets and 27 cm$^3$ of water and is added to the above solution. The mixture is stirred at a temperature close to 20° C. for 48 hours. The precipitate is filtered off on a No. 4 glass sinter and washed with 3 times 20 cm$^3$ of acetonitrile and then dried in air for 24 hours. 14.5 g of sodium salt of N-(2-chloronicotinoyl)piperidine-2-carboxylic acid are thus obtained, melting at a temperature higher than 260° C.

2-Chlorocrotononitrile can be prepared according to J. C. Pommelet, C. Nyns, F. F. Lahousse, R. Merenyl and H. G. Viehe, Angew. Chem. Int. Ed. 21, 585 (1981).

Ethyl N-(2-chloronicotinoyl)piperidine-2-carboxylate can be prepared by the method described in European Patent Application EP 124384, but from 44.7 g of ethyl piperidine-2-carboxylate and 50 g of 2-chloronicotinoyl chloride. 86.4 g of ethyl N-(2-chloronicotinoyl)piperidine-2-carboxylate are thus obtained in the form of an orange oil. (Rf=1.59; thin layer chromatography on silica gel; ethyl acetate eluent).

Example 2

A solution of 2.81 g of 2-methyl-3-(2-chloro-3-pyridyl)-5,6,7,8-tetrahydroindolizine-1-carbonitrile in 56.2 cm$^3$ of 12N hydrochloric acid (d=1.19) is heated with stirring at a temperature of approximately 90° C. for 1 hour and 30 minutes. The green-coloured solution obtained is then concentrated at reduced pressure (2.7 kPa) at a temperature close to 60° C. The residual oil is dissolved in 150 cm$^3$ of chloroform and stirred vigorously with 100 cm$^3$ of an aqueous solution of sodium bicarbonate at a concentration of 5%. The solution obtained is colourless. The organic phase is washed 3 times with 40 cm$^3$ of water. The organic extracts are combined and dried over anhydrous sodium sulphate, filtered and concentrated to dryness at reduced pressure (2.7 kPa) at a temperature close to 50° C. A translucent oil is thus obtained which is taken up in 20 cm$^3$ of isopropanol. The solution is cooled to approximately 0° C. The crystals which appear are separated off by filtration and washed with 3 times 2 cm$^3$ of isopropanol at 0° C. 1.71 g of 2-methyl-3-(2-chloro-3-pyridyl)-5,6,7,8-tetrahydroindolizine-1-carbonitrile which has not reacted are thus collected. The filtrate and the washing solutions are combined and dried to dryness at reduced pressure (2.7 kPa) at a temperature close to 50° C. 1.1 g of product is thus obtained which is chromatographed on a column of 1.4 cm diameter containing 60 g of silica (0.04–0.0063). Elution is carried out with ethyl acetate at a total pressure of 1.5 bar, 20-cm$^3$ fractions being collected. The homogeneous fractions are combined and concentrated at reduced pressure (2.7 kPa) at a temperature close to 60° C. 0.32 g of 2-methyl-3-(2-chloro-3-pyridyl)-5,6,7,8-tetrahydroindolizine-1-carboxamide are thus obtained in the form of of white crystals melting at about 202° C.

Example 3

3-(2-Chloro-3-pyridyl)-5,6,7,8-tetrahydroindolizine-1-carbonitrile is prepared as described in Example 1, from 10 g of the sodium salt of N-(2-chloronicotinoyl)piperidine-2-carboxylic acid and 5.94 g of 2-chloroacrylonitrile. 6.6 g of 3-(2-chloro-3-pyridyl)-5,6,7,8-tetrahydroindolizine-1-carbonitrile are thus obtained in the form of white powder melting at 164° C.

The sodium salt of N-(2-chloronicotinoyl)piperidine-2-carboxylic acid can be prepared as described in Example 1.

Example 4

3-(2-Chloro-3-pyridyl)-5,6,7,8-tetrahydroindolizine-1-carboxamide is prepared as described in Example 2, from 3 g of 3-(2-chloro-3-pyridyl)-5,6,7,8-tetrahydroindolizine-1-carbonitrile. 2.29 g of 3-(2-chloro-3-pyridyl)-5,6,7,8-tetrahydroindolizine-1-carboxamide are thus obtained in the form of beige powder melting at 199° C.

Example 5

3-(2-Fluoro-3-pyridyl)-5,6,7,8-tetrahydroindolizine-1-carboxamide is prepared as described in Example 2, from 1.7 g of 3-(2-fluoro-3-pyridyl)-5,6,7,8-tetrahydroindolizine-1-carbonitrile. 1.2 g of 3-(2-fluoro-3-pyridyl)-5,6,7,8-tetrahydroindolizine-1-carboxamide are thus obtained in the form of beige powder melting at 190° C.

3-(2-Fluoro-3-pyridyl)-5,6,7,8-tetrahydroindolizine-1-carbonitrile is prepared as described in Example 1, from 4 g of the sodium salt of N-(2-fluoronicotinoyl)piperidine-2-carboxylic acid and 1.31 g of 2-chloroacrylonitrile. 3.2 g of 3-(2-fluoro-3-pyridyl)-5,6,7,8-tetrahydroindolizine-1-carbonitrile are thus obtained in the form of orange oil, which crystallizes (Rf=0.72; thin layer chromatography on silica gel; ethyl acetate eluent).

The sodium salt of N-(2-fluoronicotinoyl)piperidine-2-carboxylic acid can be prepared as described in Example 1, from 11.48 g of ethyl N-(2-fluoronicotinoyl)piperidine-2-carboxylate. 9 g of the sodium salt of N-(2-fluoronicotinoyl)piperidine-2-carboxylic acid are thus obtained in the form of white powder melting at a temperature higher than 260° C.

Ethyl N-(2-fluoronicotinoyl)piperidine-2-carboxylate can be prepared as follows:

23 cm$^3$ of triethylamine are added with stirring to a solution of 21.15 g of 2-fluoronicotinic acid in 500 cm$^3$ of tetrahydrofuran. The mixture is cooled with an ice and acetone bath at –8° C. 20.48 g of isobutyl chloroformate are run in dropwise over 15 minutes while the temperature is maintained at –5° C. The mixture is stirred for 15 minutes at –5° C. and the temperature is then allowed to rise again to 5° C. A solution of 23.58 g of ethyl piperidine-2-carboxylate in 100 cm$^3$ of tetrahydrofuran is added dropwise over 15 minutes. The mixture is stirred for 1 hour at 5° C. and then 12 hours at ambient temperature. Insoluble material is filtered off on a No.3 glass sinter, the cake is washed with 3 times 25 cm$^3$ of chloroform. The filtrate and the washing phases are combined and evaporated to dryness at reduced pressure (2.7 kPa) at a temperature close to 50° C. The residue is taken up with 250 cm$^3$ of ethyl acetate and washed 3 times with 200 cm$^3$ of water. The organic extracts are combined and dried over anhydrous magnesium sulphate, filtered and concentrated to dryness at reduced pressure (2.7 kPa) at a temperature close to 50° C. 35 g of a mixture of products are thus obtained and are chromatographed on a column of 8.5 cm diameter containing 1 kg of silica (0.04–0.0063). Elution is carried out with ethyl acetate at a total pressure of 1.5 bar and with 100-cm$^3$ fractions being collected. Fractions from 4 to 16 are combined and concentrated at reduced pressure (2.7 kPa) at a temperature close to 60° C. 12.8 g of ethyl N-(2-fluoronicotinoyl)piperidine-2-carboxylate are thus obtained in the form of a yellow oil (Rf=0.42; thin layer chromatography on silica gel; ethyl acetate eluent).

Example 6

2-Methyl-3-(2-fluoro-3-pyridyl)-5,6,7,8-tetrahydroindolizine-1-carboxamide is prepared as described in Example 2, from 2.77 g of 2-methyl-3-(2-fluoro-3-pyridyl)-5,6,7,8-tetrahydroindolizine-1-carbonitrile. 1.7 g of 2-methyl-3-(2-fluoro-3-pyridyl)-5,6,7,8-tetrahydroindolizine-1-carboxamide are thus obtained in the form of beige powder melting at 197° C.

2-Methyl-3-(2-fluoro-3-pyridyl)-5,6,7,8-tetrahydroindolizine-1-carbonitrile is prepared as described in Example 1, from 4.13 g of the sodium salt of N-(2-fluoronicotinoyl)piperidine-2-carboxylic acid and 1.47 g of 2-chlorocrotononitrile. 3.35 g of 2-methyl-3-(2-chloro-3-pyridyl)-5,6,7,8-tetrahydroindolizine-1-carbonitrile are thus obtained in the form of orange oil, which crystallizes (Rf=0.47; thin layer chromatography on silica gel; ethyl acetate eluent).

The sodium salt of N-(2-fluoronicotinoyl)piperidine-2-carboxylic acid can be prepared as described in Example 5.

Example 7

3-(4-Pyridyl)-5,6,7,8-tetrahydroindolizine-1-carboxamide is prepared as described in Example 2 from 3.35 g of 3-(4-pyridyl)-5,6,7,8-tetrahydroindolizine-1-carbonitrile. 1.65 g of 3-(4-pyridyl)-5,6,7,8-tetrahydroindolizine-1-carboxamide are thus obtained in the form of white powder melting at 205° C.

3-(4-Pyridyl)-5,6,7,8-tetrahydroindolizine-1-carbonitrile is prepared as described in Example 1, from 5.5 g of the sodium salt of N-(4-pyridylcarbonyl)piperidine-2-carboxylic acid and 1.97 g of 2-chloroacrylonitrile. 4.1 g of 3-(4-pyridyl)-5,6,7,8-tetrahydroindolizine-1-carbonitrile are thus prepared in the form of brown oil, which crystallizes. (Rf=0.20; thin layer chromatography on silica gel; ethyl acetate eluent).

The sodium salt of N-(4-pyridylcarbonyl)piperidine-2-carboxylic acid is prepared as described in Example 1, from 40.1 g of ethyl N-(4-pyridylcarbonyl)piperidine-2-carboxylate. 10.6 g of the sodium salt of N-(4-pyridylcarbonyl)piperidine-2-carboxylic acid are thus obtained in the form of orange oil (Rf=1.54; thin layer chromatography on silica gel; eluent: chloroform, methanol, aqueous ammonia, 12/6/1 by volume).

Ethyl N-(4-pyridylcarbonyl)piperidine-2-carboxylate can be prepared as described in Example 5, from 29.5 g of ethyl 2-piperidinecarboxylate and 18.5 g of 4-pyridinecarboxylic acid. 12.8 g of ethyl N-(4-pyridylcarbonyl)piperidine-2-carboxylate are thus obtained in the form of a yellow oil. (Rf=0.42; thin layer chromatography on silica gel; ethyl acetate eluent).

Example 8

2-Methyl-3-(4-pyridyl)-5,6,7,8-tetrahydroindolizine-1-carboxamide is prepared as described in Example 2, from 3.5 g of 2-methyl-3-(4-pyridyl)-5,6,7,8-tetrahydroindolizine-1-carbonitrile. 1.57 g of 2-methyl-3-(4-pyridyl)-5,6,7,8-tetrahydroindolizine-1-carboxamide are thus obtained in the form of cream powder melting at 268° C.

2-Methyl-3-(4-pyridyl)-5,6,7,8-tetrahydroindolizine-1-carbonitrile is prepared as described in Example 1, from 5.4 g of the sodium salt of N-(4-pyridylcarbonyl)piperidine-2-carboxylic acid and from 2.13 g of 2-chlorocrotononitrile. 3.5 g of 2-methyl-3-(4-pyridyl)-5,6,7,8-tetrahydroindolizine-1-carbonitrile are thus obtained in the form of chestnut-brown oil. (Rf=0.17; thin layer chromatography on silica gel; ethyl acetate eluent).

The sodium salt of N-(4-pyridylcarbonyl)piperidine-2-carboxylic acid is prepared as described in Example 7.

Example 9

2.42 g of N-bromosuccinimide are added with stirring to a solution of 3.5 g of 3-(2-chloro-3-pyridyl)-5,6,7,8-tetrahydroindolizine-1-carbonitrile in 50 cm³ of 1,2-dichloroethane. The mixture is refluxed for 20 hours. After cooling, the reaction mixture is concentrated at reduced pressure (2.7 kPa) at a temperature close to 60° C. The residue is taken up with 100 cm³ of ethyl acetate and washed 3 times with 70 cm³ of an aqueous solution of sodium bicarbonate at a concentration of 5%. The organic extracts are combined and dried over anhydrous magnesium sulphate, filtered and concentrated to dryness at reduced pressure (2.7 kPa) at a temperature close to 50° C. A mixture of products is thus obtained, which is chromatographed on a column of 1.8 cm diameter containing 90 g of silica (0.04–0.0063). Elution is carried out with dichloromethane at a total pressure of 1.5 bar and with 20-cm³ fractions being collected. The homogeneous fractions are combined and concentrated at reduced pressure (2.7 kPa) at a temperature close to 60° C. 2.79 g of 2-bromo-3-(3-pyridyl)-5,6,7,8-tetrahydroindolizine-1-carbonitrile are thus obtained in the form of white crystals melting at 188° C.

3-(2-Chloro-3-pyridyl)-5,6,7,8-tetrahydroindolizine-1-carbonitrile is prepared as described in Example 3.

Example 10

A solution of 1.8 g of 2-bromo-3-(2-fluoro-3-pyridyl)-5,6,7,8-tetrahydroindolizine-1-carbonitrile in 8 cm³ of 60% sulphuric acid is heated with stirring at a temperature of approximately 80° C. for 5 hours. The solution obtained is run into 100 cm³ of a saturated solution of sodium bicarbonate. The aqueous phase is extracted with 3 times 100 cm³ of dichloromethane. The organic extracts are combined and dried over anhydrous magnesium sulphate, filtered and concentrated to dryness at reduced pressure (2.7 kPa) at a temperature close to 50° C. 1.7 g of product are thus obtained and are chromatographed on a column of 1.8 cm diameter containing 90 g of silica (0.04–0.0063). Elution is carried out with ethyl acetate at a total pressure of 1.5 bar, 20-cm³ fractions being collected. Fractions from 17 to 32 are combined and concentrated at reduced pressure (2.7 kPa) at a temperature close to 60° C. 0.88 g of 2-bromo-3-(2-fluoro-3-pyridyl)-5,6,7,8-tetrahydroindolizine-1-carboxamide are thus obtained in the form of of white crystals melting at 202° C.

2-Bromo-3-(2-fluoro-3-pyridyl)-5,6,7,8-tetrahydroindolizine-1-carbonitrile is prepared as described in Example 9, from 1.6 g of 3-(2-fluoro-3-pyridyl)-5,6,7,8-tetrahydroindolizine-1-carbonitrile and 1.3 g of N-bromosuccinimide. 1.8 g of 2-bromo-3-(2-fluoro-3-pyridyl)-5,6,7,8-tetrahydroindolizine-1-carbonitrile are thus obtained in the form of beige powder melting at 172° C.

3-(2-Fluoro-3-pyridyl)-5,6,7,8-tetrahydroindolizine-1-carbonitrile is prepared as described in Example 5.

Example 11

2.3 g of an aqueous solution of potassium hydroxide at a concentration of 85% are added to a solution of 3 g of 2-bromo-3-(4-pyridyl)-5,6,7,8-tetrahydroindolizine-1-carbonitrile in 30 cm³ of isopropanol. The mixture is refluxed for 5 days. The solution obtained is run into 50 cm³ of water. The mixture is filtered on a No. 3 glass sinter and the cake is washed with 3 times 15 cm³ of water and then dried at 100° C. 1.1 g of product is thus obtained, which is recrystallized from a mixture of 80 cm³ of methanol and 3 cm³ of dimethylformamide. 0.63 g of 2-bromo-3-(4-pyridyl)-5,6,7,8-tetrahydroindolizine-1-carboxamide are thus obtained in the form of pale yellow crystals melting at a temperature higher than 260° C. (Rf=0.25; thin layer chromatography on silica gel; eluent: ethyl acetate/methanol, 9/1 by volume).

2-Bromo-3-(4-pyridyl)-5,6,7,8-tetrahydroindolizine-1-carbonitrile is prepared as described in Example 9, from 2.2 g [lacuna] 3-(4-pyridyl)-5,6,7,8-tetrahydroindolizine-1-carbonitrile and 2.26 g of N-bromosuccinimide. 2.5 g of 2-bromo-3-(4-pyridyl)-5,6,7,8-tetrahydroindolizine-1-carbonitrile are thus obtained in the form of orange-beige powder melting at 120° C.

3-(4-Pyridyl)-5,6,7,8-tetrahydroindolizine-1-carbonitrile is prepared as described in Example 7.

Example 12

5-(2-Chloro-3-pyridyl)-2,3-dihydropyrrolo[2,1-b]thiazole-7-carbonitrile is prepared by the method described in European Patent Application EP 147317, but from 32.3 g of N-(2-chloronicotinoyl)thiazolidine-2-carboxylic acid. 11.6 g of 5-(2-chloro-3-pyridyl)-2,3-dihydropyrrolo[2,1-b]thiazole-7-carbonitrile are thus obtained in the form of a pink powder melting at 172° C.

N-(2-Chloronicotinoyl)thiazolidine-2-carboxylic acid is prepared by the method described in European Patent Application EP 147317, but from 21.31 g of thiazolidine-2-carboxylic acid and 28.8 g of 2-chloronicotinoyl chloride hydrochloride. 40.1 g of N-(2-chloronicotinoyl)thiazolidine-2-carboxylic acid are thus obtained in the form of white solid foam.

Example 13

5-(2-Chloro-3-pyridyl)-2,3-dihydropyrrolo[2,1-b]thiazole-7-carboxamide is prepared as in Example 2, from 3 g of 5-(2-chloro-3-pyridyl)-2,3-dihydropyrrolo[2,1-b]thiazole-7-carbonitrile. 2.75 g of 5-(2-chloro-3-pyridyl)-2,3-dihydropyrrolo[2,1-b]thiazole-1-carboxamide are thus obtained in the form of white crystals melting at 244° C.

Example 14

6-Bromo-5-(3-pyridyl)-1H,3H-pyrrolo[1,2-c]thiazole-7-carbonitrile is prepared as in Example 9, from 5 g of 5-(3-pyridyl)-1H,3H-pyrrolo[1,2-c]thiazole-7-carbonitrile and 4.1 g of N-bromosuccinimide. 2.07 g of 6-bromo-5-(3-pyridyl)-1H,3H-pyrrolo[1,2-c]thiazole-7-carbonitrile are thus obtained in the form of white powder melting at 190° C.

5-(3-Pyridyl)-1H,3H-pyrrolo[1,2-c]thiazole-7-carbonitrile is described in European Patent Application EP 147317.

Example 15

A solution of 42.4 g of sulphonyl isocyanate chloride in 150 cm³ of acetonitrile is added to a suspension of 22.7 g of 5-(3-pyridyl)-1H,3H-pyrrolo[1,2-c]thiazole-6-carbonitrile in 1500 cm³ of acetonitrile, cooled with an ice and acetone bath at −10° C. and under argon atmosphere. The addition is performed over 40 minutes and the temperature is maintained at 5° C. The mixture becomes homogeneous and the stirring is maintained for 12 hours at ambient temperature. The mixture is then hydrolysed in a 3-litre conical flask containing crushed ice. The pH of the solution is brought to pH 9 with sodium hydroxide in a mass concentration of 30%. The aqueous phase is extracted with 3 times 500 cm³ of ethyl acetate. The organic extracts are combined and dried over magnesium sulphate, filtered and concentrated to dryness at reduced pressure (2.7 kPa) at a temperature close to 50° C. 12.8 g of product are thus obtained and are chromatographed on a column of 5 cm diameter containing 800 g of silica (0.04–0.0063). Elution is carried out with ethyl acetate at a total pressure of 1.5 bar and with 100-cm³ fractions being collected. Fractions from 70 to 90 are combined and concentrated at reduced pressure (2.7 kPa) at a temperature close to 60° C. 0.24 g of a product are thus obtained and are taken up with 35 cm³ of dichloromethane and vegetable charcoal. The solution is filtered on a No. 4 glass sinter and then concentrated to dryness at reduced pressure (2.7 kPa) at a temperature close to 50° C. 0.21 g of 6-cyano-5-(3-pyridyl)-1H,3H-pyrrolo[1,2-c]thiazole-7-carboxamide are thus obtained in the form of a beige powder melting at 217° C.

5-(3-Pyridyl)-1H,3H-pyrrolo[1,2-c]thiazole-6-carbonitrile is obtained from the 85/15 mixture of 5-(3-pyridyl)-1H,3H-pyrrolo[1,2-c]thiazole-7-carbonitrile and of 5-(3-pyridyl)-1H,3H-pyrrolo[1,2-c]thiazole-6-carbonitrile, the preparation of which is described in European Patent Application EP 147317. A mixture of 28.47 g of 5-(3-pyridyl)-1H,3H-pyrrolo[1,2-c]thiazole-7-carbonitrile and 6-carbonitrile is chromatographed on a column of 5 cm diameter containing 800 g of silica (0.04–0.0063). Elution is carried out with ethyl acetate at a total pressure of 1.5 bar and with 100-cm³ fractions being collected. Fractions from 70 to 90 are combined and concentrated at reduced pressure (2.7 kPa) at a temperature close to 60° C. 2.65 g of 5-(3-pyridyl)-1H,3H-pyrrolo[1,2-c]thiazole-6-carbonitrile (Rf=0.38; thin layer chromatography on silica gel; ethyl acetate eluent) and 19.5 g of a 93/7 mixture of 7-carbonitrile and 6-carbonitrile, are thus obtained.

Example 16

6-Methyl-5-(5-thiazolyl)-1H,3H-pyrrolo[1,2-c]thiazole-7-carboxamide is prepared as described in Example 2, from 4.5 g of a 65/35 mixture of 6-methyl-5-(5-thiazolyl)-1H,3H-pyrrolo[1,2-c]thiazole-7-carbonitrile and of 7-methyl-5-(5-thiazolyl)-1H,3H-pyrrolo[1,2-c]thiazole-6-carbonitrile. 0.35 g of 6-methyl-5-(5-thiazolyl)-1H,3H-pyrrolo[1,2-c]thiazole-7-carboxamide are thus obtained in the form of white powder melting at 247° C.

The mixture of 6-methyl-5-(5-thiazolyl)-1H,3H-pyrrolo[1,2-c]thiazole-7-carbonitrile and of 7-methyl-5-(5-thiazolyl)-1H,3H-pyrrolo[1,2-c]thiazole-6-carbonitrile is prepared as described in Example 1, from 48.8 g of N-(5-thiazolylcarbonyl)thiazolidine-4-carboxylic acid and 40.6 g of 2-chlorocrotononitrile. A 65/35 mixture of 6-methyl-5-(5-thiazolyl)-1H,3H-pyrrolo[1,2-c]thiazole-7-carbonitrile and of 7-methyl-5-(5-thiazolyl)-1H,3H-pyrrolo[1,2-c]thiazole-6-carbonitrile (according to the NMR spectrum) is thus obtained (Rf=0.72; thin layer chromatography on silica gel; ethyl acetate eluent).

N-(5-Thiazolylcarbonyl)thiazolidine-4-carboxylic acid is described in European Patent Application EP 147317.

Example 17

6-Methyl-5-(2-chloro-3-pyridyl)-1H-2,3-dihydropyrrolizine-7-carbonitrile is prepared by the method described in European Patent Application EP 118321, but from 4.36 g of N-(2-chloronicotinoyl)proline-4-carboxylic acid and 17.25 g of 2-chlorocroto-nonitrile. 40 mg of 6-methyl-5-(2-chloro-3-pyridyl)-1H-2,3-dihydropyrrolizine-7-carbonitrile are thus obtained in the form of a yellowish solid melting at about 136° C.

N-(2-Chloronicotinoyl)-L-proline-4-carboxylic acid is prepared as described in Example 5 from 3.65 g of L-proline-4-carboxylic acid and 5 g of 2-chloronicotinic acid. 5.36 g of N-(2-chloronicotinoyl)proline-4-carboxylic acid are thus obtained in the form of yellow oil. (Rf=0.25; thin layer chromatography on silica gel; eluent: ethyl acetate/acetic acid, 80/20 by volume).

Example 18

6-Methyl-5-(2-hydroxy-3-pyridyl)-1H-2,3-dihydropyrrolizine-7-carboxamide is prepared as described in Example 2, from 1.5 g of 6-methyl-5-(2-fluoro-3-pyridyl)-1H-2,3-dihydropyrrolizine-7-carbonitrile. 0.22 g of 6-methyl-5-(2-hydroxy-3-pyridyl)-1H-2,3-dihydropyrrolizine-7-carboxamide are thus obtained in the form of white powder melting at 315° C.

6-Methyl-5-(2-fluoro-3-pyridyl)-1H-2,3-dihydropyrrolizine-7-carbonitrile is prepared as described in Example 1, from 7.63 g of N-(2-fluoronicotinoyl)proline-4-carboxylic acid and 6.5 g of 2-chlorocrotononitrile. 1.4 g of 6-methyl-5-(2-fluoro-3-pyridyl)-1H-2,3-dihydropyrrolizine-7-carbonitrile are thus obtained in the form of white crystals melting at 100° C.

N-(2-Fluoronicotinoyl)-L-proline-4-carboxylic acid is prepared as described in Example 5, from 5 g of 2-fluoronicotinic acid and from 4.07 g of L-proline. 5.15 g of N-(2-fluoronicotinoyl)-L-proline-4-carboxylic acid are thus obtained and used as such in the following reaction.

Example 19

6-Methyl-5-(2-fluoro-3-pyridyl)-1H,3H-pyrrolo[1,2-c]thiazole-7-carbonitrile is prepared as described in Example 1, from 4 g of N-(2-fluoronicotinoyl)thiazole-4-carboxylic acid and from 2.95 g of 2-chlorocrotononitrile. 1.56 g of 6-methyl-5-(2-fluoro-3-pyridyl)-1H,3H-pyrrolo[1,2-c]thiazole-7-carbonitrile are thus obtained in the form of yellow crystals melting at 132° C.

N-(2-Fluoronicotinoyl)thiazole-4-carboxylic acid is prepared as described in Example 5 from 11.03 g of thiazole-4-carboxylic acid and 11.7 g of 2-fluoronicotinic acid. 8.7 g of N-(2-fluoronicotinoyl)thiazole-4-carboxylic acid are thus obtained in the form of a cream solid. (Rf=0.33; thin layer chromatography on silica gel; eluent: ethyl acetate/acetic acid, 90/10 by volume).

Example 20

7-Methyl-6-(2-fluoro-3-pyridyl)-1,2-dihydro-4H-pyrrolo[1,2-c]-1,3-thiazine-8-carboxamide is prepared as described in Example 10, from 3.85 g of 7-methyl-6-(2-fluoro-3-pyridyl)-1,2-dihydro-4H-pyrrolo[1,2-c]-1,3-thiazine-8-carbonitrile. 1.5 g of 7-methyl-6-(2-fluoro-3-pyridyl)-1,2-dihydro-4H-pyrrolo[1,2-c]-1,3-thiazine-8-carboxamide are thus obtained in the form of light-yellow crystals melting at 213° C.

7-Methyl-6-(2-fluoro-3-pyridyl)-1,2-dihydro-4H-pyrrolo[1,2-c]-1,3-thiazine-8-carbonitrile is prepared as described in Example 1, but from 6.6 g of N-(2-fluoronicotinoyl)-3,4,5,6-tetrahydro-2H-1,3-thiazine-4-carboxylic acid and 4.95 g of 2-chlorocrotononitrile. 3.4 g of 7-methyl-6-(2-fluoro-3-pyridyl)-1,2-dihydro-4H-pyrrolo[1,2-c]-1,3-thiazine-8-carbonitrile are thus obtained in the [lacuna] of white crystals melting at 122° C.

N-(2-Fluoronicotinoyl)-2H-3,4,5,6-tetrahydro-1,3-thiazine-4-carboxylic acid is prepared by the method described in European Patent Application EP 118321, but from 8.2 g of ethyl N-(2-fluoronicotinoyl)-3,4,5,6-tetrahydro-2H-1,3-thiazine-4-carboxylate. 6.6 g of N-(2-fluoronicotinoyl)-3,4,5,6-tetrahydro-2H-1,3-thiazine-4-carboxylic acid are thus obtained in the form of yellow crystals melting at 179° C.

Ethyl N-(2-fluoronicotinoyl)-3,4,5,6-tetrahydro-2H-1,3-thiazine-4-carboxylate is prepared by the method described in European Patent Application EP 118321, but from 12.5 g of ethyl 3,4,5,6-tetrahydro-2H-1,3-thiazine-4-carboxylate hydrochloride and 13.5 g of 2-fluoronicotinic acid. 8.2 g of ethyl N-(2-fluoronicotinoyl)-3,4,5,6-tetrahydro-2H-1,3-thiazine-4-carboxylate are thus obtained in the form of light-yellow oil, employed as such in the following reaction.

Ethyl 3,4,5,6-tetrahydro-2H-1,3-thiazine-4-carboxylate hydrochloride is described in European Patent Application EP 118321.

Example 21

7-Methyl-6-(2-chloro-3-pyridyl)-1,2-dihydro-4H-pyrrolo[1,2-c]-1,3-thiazine-8-carboxamide is prepared as described in Example 10 from 3.2 g of 7-methyl-6-(2-chloro-3-pyridyl)-1,2-dihydro-4H-pyrrolo[1,2-c]-1,3-thiazine-8-carbonitrile. 0.7 g of 7-methyl-6-(2-chloro-3-pyridyl)-1,2-dihydro-4H-pyrrolo[1,2-c]-1,3-thiazine-8-carboxamide are thus obtained in the form of light-beige powder melting at 215° C.

7-Methyl-6-(2-chloro-3-pyridyl)-1,2-dihydro-4H-pyrrolo[1,2-c]-1,3-thiazine-8-carbonitrile is prepared as described in Example 1, from 14.3 g of N-(2-chloronicotinoyl)-3,4,5,6-tetrahydro-2H-1,3-thiazine-4-carboxylic acid and 10 g of 2-chlorocrotononitrile. 3.8 g of 7-methyl-6-(2-chloro-3-pyridyl)-1,2-dihydro-4H-pyrrolo[1,2-c]-1,3-thiazine-8-carbonitrile are thus obtained in the form of cream powder melting at 168° C.

N-(2-Chloronicotinoyl)-3,4,5,6-tetrahydro-2H-1,3-thiazine-4-carboxylic acid is prepared by the method described in European Patent Application EP 118321, but starting from 16 g of ethyl N-(2-chloronicotinoyl)-3,4,5,6-tetrahydro-2H-1,3-thiazine-4-carboxylate. 12.7 g of N-(2-chloronicotinoyl)-3,4,5,6-tetrahydro-2H-1,3-thiazine-4-carboxylic acid are thus obtained in the form of white powder melting at 200° C.

Ethyl N-(2-chloronicotinoyl)-3,4,5,6-tetrahydro-2H-1,3-thiazine-4-carboxylate is prepared by the method described in European Patent Application EP 118321, but from 16.5 g of ethyl 3,4,5,6-tetrahydro-2H-1,3-thiazine-4-carboxylate hydrochloride and 18.8 g of 2-chloronicotinic acid. 8.2 g of ethyl N-(2-fluoronicotinoyl)-3,4,5,6-tetrahydro-2H-1,3-thiazine-4-carboxylate are thus obtained in the form of light-yellow oil, employed as such in the following reaction.

Ethyl 2H-3,4,5,6-tetrahydro-1,3-thiazine-4-carboxylate hydrochloride is described in European Patent Application EP 118321.

Example 22

5-(2-Chloro-3-pyridyl)-1H,3H-pyrrolo[1,2-c]thiazole-7-carboxamide is prepared as described in Example 11, from 4.7 g of 5-(2-chloro-3-pyridyl)-1H,3H-pyrrolo[1,2-c]thiazole-7-carbonitrile. 3 g of 5-(2-chloro-3-pyridyl)-1H,3H-pyrrolo[1,2-c]thiazole-7-carboxamide are thus obtained in the form of cream powder melting at 264° C.

5-(2-chloro-3-pyridyl)-1H,3H-pyrrolo[1,2-c]thiazole-7-carbonitrile is prepared by the method described in European Patent Application EP 147317, but from 19 g of N-(2-chloronicotinoyl)thiazolidine-4-carboxylic acid and from 61 g of 2-chloroacrylonitrile. 4.7 g of 5-(2-chloro-3-pyridyl)-1H,3H-pyrrolo[1,2-c]thiazole-7-carbonitrile are thus obtained in the form of ochre powder melting at 167° C.

N-(2-Chloronicotinoyl)thiazolidine-4-carboxylic acid is prepared as described in Example 5, from 27 g of ethyl N-(2-chloronicotinoyl)thiazolidine-4-carboxylate. 19.3 g of N-(2-chloronicotinoyl)thiazolidine-4-carboxylic acid are thus obtained in the form of an orangy resin, employed crude.

Ethyl N-(2-chloronicotinoyl)thiazolidine-4-carboxylate is prepared as described in Example 5, from 23 g of ethyl L-thiazolidine-4-carboxylate hydrochloride and 20.4 g of 2-chloronicotinoyl chloride. 27 g of ethyl N-(2-chloronicotinoyl)thiazolidine-4-carboxylate are thus obtained in the form of a yellow oil, employed crude.

Example 23

A mixture of 18.5 g of 3-(3-pyridyl)-5,6,7,8-tetrahydroindolizine-1-carbonitrile and of 14.8 g of N-bromosuccinimide in 400 cm³ of ethyl acetate is stirred at a temperature close to 20° C. for 2 hours. The reaction mixture is then concentrated at reduced pressure (2.7 kPa) at a temperature close to 40° C. and 40.95 g of residue are chromatographed on a column of 8 cm diameter containing 1 kg of silica (0.04–0.0063). Elution is carried out with a 98/2 mixture by volume of dichloromethane and of methanol, at a total pressure of 1.5 bar and with 100-cm³ fractions being collected. The homogeneous fractions are combined and concentrated at reduced pressure (2.7 kPa) at a temperature close to 40° C. 28.3 g of a white solid are thus obtained and this is then beaten in 200 cm³ of ethyl ether. After filtration and washing of the insoluble solid with ethyl ether and then with pentane, 21.5 g of 2-bromo-3-(3-pyridyl)-5,6,7,8-tetrahydroindolizine-1-carbonitrile are obtained in the form of a white powder melting at 167° C.

3-(3-Pyridyl)-5,6,7,8-tetrahydroindolizine-1-carbonitrile is prepared as described in European Patent Application EP 124383.

Example 24

A suspension of 3.0 g of 2-bromo-3-(3-pyridyl)-5,6,7,8-tetrahydroindolizine-1-carbonitrile prepared from 4.2 g of potassium hydroxide pellets in 60 cm³ of tert-butyl alcohol is heated at 90° C. for 20 hours. 120 cm³ of water and 120 cm³ of ethyl acetate are then added to the reaction mixture. The organic phase is then separated off and the aqueous phase extracted with 100 cm³ of ethyl acetate. The combined organic phases are washed with 100 cm³ of water, dried over magnesium sulphate and then concentrated at reduced pressure (2.7 kPa) at a temperature close to 40° C., to give a solid residue (1.7 g). The latter is beaten in an ethyl ether (10 cm³)/pentane (10 cm³) mixture. After filtration and washing of the insoluble fraction with pentane, 1.35 g of 2-bromo-3-(3-pyridyl)-5,6,7,8-tetrahydroindolizine-1-carboxamide are obtained in the form of a white powder melting at 220° C.

Example 25

A mixture of 1.1 g of 3-(3-pyridyl)-5,6,7,8-tetrahydroindolizine-1-carbonitrile and of 1.1 g of N-iodosuccinimide in 20 cm³ of 1,2-dichloroethane is heated to reflux for 18 hours. 1.1 g of N-iodosuccinimide are then added to the reaction mixture and the resulting mixture is heated to reflux for an additional 24 hours. 20 cm³ of water are added to the reaction mixture. The organic phase is then separated off and the aqueous phase extracted with 20 cm³ of dichloromethane. The combined organic phases are washed with 50 cm³ of water, dried over magnesium sulphate and then concentrated at reduced pressure (2.7 kPa) at a temperature close to 40° C., to give a solid residue (1.5 g). The latter is beaten in 50 cm³ of ether. After filtration and washing of the insoluble fraction with pentane 1.19 g of solid are obtained. This residue is chromatographed on a column of 4 cm diameter containing 140 g of silica (0.04–0.0063). Elution is carried out with a 98/2 by volume mixture of dichloromethane and methanol, at a total pressure of 1.5 bar and with 50-cm³ fractions being collected. The homogeneous fractions are combined and concentrated at reduced pressure (2.7 kPa) at a temperature close to 40° C. 0.77 g of yellow solid are thus obtained, and this is then recrystallized from 25 cm³ of ethyl acetate to give, after filtration and washing of the crystals with ethyl acetate (5 cm³) and then with 2 times 10 cm³ of pentane, 0.39 g of 2-iodo-3-(3-pyridyl)-5,6,7,8-tetrahydroindolizine-1-carbonitrile in the form of a pale-yellow powder melting at 208° C.

3-(3-Pyridyl)-5,6,7,8-tetrahydroindolizine-1-carbonitrile is prepared as described in European Patent Application EP 124383.

Example 26

A quantity of 2.45 g of 2-iodo-3-(3-pyridyl)-5,6,7,8-tetrahydroindolizine-1-carbonitrile is hydrolysed according to Example 24 by employing 3 g of potassium hydroxide pellets in 50 cm³ of tert-butyl alcohol. After purification by chromatography (column diameter 4 cm; 125 g of silica; 50-cm³ fractions; elution with a 97/3 dichloromethane/methanol mixture), 0.91 g of 2-iodo-3-(3-pyridyl)-5,6,7,8-tetrahydroindolizine-1-carboxamide are thus obtained in the form of a powder melting at 243° C.

Example 27

2-Methyl-3-(3-pyridyl)-5,6,7,8-tetrahydroindolizine-1-carbonitrile is prepared as described in Example 1, from 11.7 g of N-nicotinoyl piperidine-2-carboxylic acid (prepared according to European Patent Application EP 118321), 10 g of paratoluenesulphonyl chloride, from 24.6 cm³ of triethylamine and from 4.8 cm³ of 2-chlorocrotononitrile. 4.3 g of 2-methyl-3-(3-pyridyl)-5,6,7,8-tetrahydroindolizine-1-carbonitrile are thus obtained in the form of a white powder melting at 125° C. 1.7 g of a 70/30 mixture of this compound and of its regioisomer, 1-methyl-3-(3-pyridyl)-5,6,7,8-tetrahydroindolizine-1-carbonitrile are also obtained.

Example 28

A quantity of 1.7 g of a mixture of regioisomers is hydrolysed according to Example 24 by employing 3 g of potassium hydroxide pellets in 34 cm³ of tert-butyl alcohol. After purification by chromatography (column diameter 4 cm; 150 g of silica; 50-cm3 fractions; elution with ethyl acetate), 0.88 g of 2-methyl-3-(3-pyridyl)-5,6,7,8-tetrahydroindolizine-1-carboxamide are finally obtained in the form of a white powder melting at 209° C.

Example 29

A mixture of 21.1 g of 2-bromo-3-( 3-pyridyl)-5,6,7,8-tetrahydroindolizine-1-carbonitrile, of 45.9 cm³ of allyltributyltin, and of 1.2 g of tetrakis-(triphenylphosphine) palladium in 70 cm³ of dimethylformamide is heated at 100° C. for 18 hours. 350 cm³ of water and 280 cm³ of dichloromethane are then added to the reaction mixture. The organic phase is then separated off and the aqueous phase extracted with 150 cm³ of dichloromethane. The combined organic phases are washed with 150 cm³ of water, dried over magnesium sulphate and then concentrated at reduced pressure (2.7 kPa), at a temperature close to 40° C., to give a solid residue (45 g). The latter is chromatographed on a column of 6 cm diameter containing 250 g of silica (0.04–0.0063). Elution is carried out with a 98/2 by volume mixture of dichloromethane and of methanol, at a total pressure of 1.5 bar and with 50-cm³ fractions being collected. The homogeneous fractions are combined and concentrated at reduced pressure (2.7 kPa) at a temperature close to 40° C. 11 g of 2-allyl-3-(3-pyridyl)-5,6,7,8-tetrahydroindolizine-1-carbonitrile are thus obtained in the form of a white powder melting at 106° C.

2-Bromo-3-(3-pyridyl)-5,6,7,8-tetrahydroindolizine-1-carbonitrile is prepared as described in Example 23.

Example 30

A quantity of 8.7 g of 2-allyl-3-(3-pyridyl)-5,6,7,8-tetrahydroindolizine-1-carbonitrile is hydrolyzed according to Example 24 by employing 13.9 g of potassium hydroxide pellets in 174 cm³ of tert-butyl alcohol. After purification by chromatography (column diameter 6 cm; 350 g of silica; 50-cm³ fractions; elution with ethyl acetate) and recrystallization from ethanol, 2.6 g of 2-(1-propenyl)-3-(3-pyridyl)-5,6,7,8-tetrahydroindolizine-1-carboxamide are thus obtained in the form of a white powder melting at 195° C.

Example 31

A mixture of 0.3 g of 2-bromo-3-(3-pyridyl)-5,6,7,8-tetrahydroindolizine-1-carbonitrile, of 1.58 cm³ of vinyltributyltin and of 1.2 g of tetrakis-(triphenylphosphine) palladium in 1 cm³ of dimethylformamide is heated at 80° C. for 18 hours. 6 cm³ of water and 3 cm³ of dichloromethane are then added to the reaction mixture. The organic phase is then separated off and the aqueous phase extracted with 5 cm³ of dichloromethane. The combined organic phases are washed with 5 cm³ of water, dried over magnesium sulphate and then concentrated at reduced pressure (2.7 kPa) at a temperature close to 40° C., to give a solid residue. The latter is beaten in an ethyl ether/pentane mixture (5 cm³/5 cm³). After filtration and washing of the insoluble fraction with pentane 0.165 g of 2-vinyl-3-(3-pyridyl)-5,6,7,8-tetrahydroindolizine-1-carbonitrile are obtained in the form of a white powder melting at 157° C.

2-Bromo-3-(3-pyridyl)-5,6,7,8-tetrahydroindolizine-1-carbonitrile is prepared as described in Example 23.

Example 32

9.7 g of 2-vinyl-3-(3-pyridyl)-5,6,7,8-tetrahydroindolizine-1-carbonitrile are hydrolysed according to Example 24 by employing 16.35 g of potassium hydroxide pellets in 200 cm³ of tert-butyl alcohol. After purification by chromatography (column diameter 6 cm; 400 g of silica; 50-cm³ fractions; elution with ethyl acetate), 5.6 g of 2-vinyl-3-(3-pyridyl)-5,6,7,8-tetrahydroindolizine-1-carboxamide are thus obtained in the form of a white powder melting at 184° C.

Example 33

A quantity of 2 g of 2-vinyl-3-(3-pyridyl)-5,6,7,8-tetrahydroindolizine-1-carboxamide is hydrogenated under pressure (1 atmosphere) at a temperature close to 20° C., in 80 cm³ of absolute ethanol in the presence of 0.2 g of 10% palladium on charcoal. After five hours' reaction, the reaction mixture is purged with nitrogen and then filtered on Celite. The insoluble cake is washed repeatedly with 3 times 20 cm³ of dichloromethane and the combined filtrates are concentrated at reduced pressure (2.7 kPa) at a temperature close to 40° C., to give 2.45 g of a solid residue. The latter is stirred in 50 cm³ of ether. After filtration and washing of the insoluble fraction with pentane 1.8 g of 2-ethyl-3-(3-pyridyl)-5,6,7,8-tetrahydroindolizine-1-carbonitrile are obtained in the form of a white powder melting at 200° C.

Example 34

A quantity of 2.3 g of a mixture containing approximately 85 mol % of 2-chloro-3-(3-pyridyl)-5,6,7,8-tetrahydroindolizine-1-carboxamide, 10 mol % of 3-(3-pyridyl)-5,6,7,8-tetrahydroindolizine-1-carboxamide and 5 mol % of 2-chloro-3-(3-pyridyl)-5,6-dihydroindolizine-1-carboxamide are hydrogenated as described in Example 33, in 70 cm³ of absolute ethanol in the presence of 0.23 g of 10% palladium on charcoal, for three hours. After three successive beatings of the final residue, in 20 cm³ of refluxing acetonitrile, 1.4 g of 2-chloro-3-(3-pyridyl)-5,6,7,8-tetrahydroindolizine-1-carboxamide are thus obtained in the form of a beige powder melting at 240° C.

A quantity of 3.45 g of a mixture containing approximately 80 mol % of 2-chloro-3-(3-pyridyl)-5,6,7,8-tetrahydroindolizine-1-carbonitrile, 15 mol % of 3-(3-pyridyl)-5,6,7,8-tetrahydroindolizine-1-carbonitrile and 5 mol % of 2-chloro-3-(3-pyridyl)-5,6-dihydroindolizine-1-carbonitrile is hydrolysed as in Example 24 by employing 3.75 g of potassium hydroxide pellets in 70 cm³ of tert-butanol. 2.4 g of a mixture containing approximately 85 mol % of 2-chloro-3-(3-pyridyl)-5,6,7,8-tetrahydroindolizine-1-carboxamide, 10 mol % of 3-(3-pyridyl)-5,6,7,8-tetrahydroindolizine-1-carboxamide and 5 mol % of 2-chloro-3-(3-pyridyl)-5,6-dihydroindolizine-1-carboxamide are thus obtained in the form of a white powder melting at 235° C.

A mixture of 11 g of 3-(3-pyridyl)-5,6,7,8-tetrahydroindolizine-1-carbonitrile prepared as described in European Patent Application EP 124383 and of 6.6 g of N-chlorosuccinimide in 220 cm³ of 1,2-dichloroethane is stirred at a temperature close to 20° C. for approximately 5 days. 100 cm³ of water are added to the reaction mixture. The organic phase is then separated off and the aqueous phase extracted with 50 cm³ of 1,2-dichloroethane. The combined organic phases are washed with 50 cm³ of water, dried over magnesium sulphate and then concentrated at reduced pressure (2.7 kPa) at a temperature close to 40° C., to give a solid residue (11.95 g). This residue is chromatographed on a column of 6 cm diameter containing 250 g of silica (0.04–0.0063). Elution is carried out with a 50/50 by volume mixture of cyclohexane and ethyl acetate at a total pressure of 1.5 bar and with 50-cm³ fractions being collected. The homogeneous fractions are combined and concentrated at reduced pressure (2.7 kPa) at a temperature close to 40° C. 3.5 g of a mixture containing approximately 80 mol % of 2-chloro-3-(3-pyridyl)-5,6,7,8-tetrahydroindolizine-1-carbonitrile, 15 mol % of 3-(3-pyridyl)-5,6,7,8-tetrahydroindolizine-1-carbonitrile and 5 mol % of 2-chloro-3-(3-pyridyl)-5,6-dihydroindolizine-1-carbonitrile are thus obtained in the form of a white powder melting at 145° C.

Example 35

A quantity of 0.45 g of 2-trifluoromethyl-3-(3-pyridyl)-5,6,7,8-tetrahydroindolizine-1-carbonitrile is hydrolysed in accordance with Example 24 by employing 0.43 g of potassium hydroxide pellets in 9 cm³ of tert-butyl alcohol. The residue obtained (0.25 g) is combined with 1.75 g of product prepared in the same way in a previous operation and then purified by chromatography (column diameter 4 cm; 150 g of silica; 50-cm³ fractions; elution with ethyl acetate). 0.95 g of white solid are thus obtained, which is then beaten in 50 cm³ of ether. After filtration and washing of the insoluble fraction with ethyl ether and then with pentane, 0.85 g of 2-trifluoromethyl-3-(3-pyridyl)-5,6,7,8-tetrahydroindolizine-1-carboxamide are obtained in the form of a white powder melting at 216° C.

2-Trifluoromethyl-3-(3-pyridyl)-5,6,7,8-tetrahydroindolizine-1-carbonitrile is prepared according to the following method:

A mixture of 6 g of 2-iodo-3-(3-pyridyl)-5,6,7,8-tetrahydroindolizine-1-carbonitrile, of 14 g of sodium trifluoroacetamide and of 6.9 g of cuprous iodide in 150 cm³ of N-methylpyrrolidone is heated under argon at a temperature close to 160° C. for 6.5 hours. The reaction mixture is then filtered and the insoluble fraction is washed with 50 cm³ of dichloromethane. The filtrate is diluted with 500 cm³ of water and 200 cm³ of dichloromethane. The precipitate which appears is then filtered off and the filtrate is decanted. The organic phase is separated from the aqueous phase and the latter is extracted with dichloromethane (100 cm³). The combined organic phases are washed again with water (100 cm³), dried over magnesium sulphate and then concentrated at reduced pressure (2.7 kPa) at a temperature close to 40° C., to give 24 g of a black oil. This residue is chromatographed on a column of 6 cm diameter containing 500 g of silica (0.04–0.0063). Elution is carried out with ethyl acetate at a total pressure of 1.5 bar and with 100-cm³ fractions being collected. The homogeneous fractions are combined and concentrated at reduced pressure (2.7 kPa) at a temperature close to 40° C. 5.5 g of solid are thus obtained which then beaten in 150 cm³ of ethyl ether. After filtration and washing with ethyl ether and then with pentane 3.8 g of 2-trifluoromethyl-3-(3-pyridyl)-5,6,7,8-tetrahydroindolizine-1-carbonitrile are obtained in the form of a white powder melting at 180° C.

2-Iodo-3-(3-pyridyl)-5,6,7,8-tetrahydroindolizine-1-carbonitrile is prepared as in Example 25.

Example 36

Hydrogen chloride gas is bubbled to saturation into a suspension of 1.0 g of 6-methyl-5-(3-pyridyl)-1H,3H-pyrrolo[1,2-c]thiazole-7-carboxylic acid in 40 cm³ of methanol at ambient temperature, and then the mixture is heated to boiling for 3 hours. A chestnut-brown solution is then obtained. The mixture is then concentrated at reduced pressure (2.7 kPa) at a temperature close to 40° C., to give a solid residue which is ground wet in ethyl ether to give 1.06 g of a chestnut-brown powder. The solid is taken up in 20 cm³ of water and extracted with 6 times 50 cm³ of ethyl ether, while the aqueous phase is maintained at pH 3–4 by optional addition of an aqueous solution of sodium bicarbonate (8% concentration). The organic phases are combined and the solution is washed successively with 25 cm³ of a saturated solution of sodium bicarbonate and 30 cm³ of water and is then dried over magnesium sulphate and evaporated to dryness at reduced pressure (2.7 kPa) at a temperature close to 30° C. to give a white solid (0.65 g). The latter is washed repeatedly on sintered glass with 3 times 2 cm³ of ethyl ether, to give 0.407 g of methyl 6-methyl-5-(3-pyridyl)-1H,3H-pyrrolo[1,2-c]thiazole-7-carboxylate in the form of white powder which melts at 91° C.

Example 37

A suspension of 5.2 g of 6-methyl-5-(3-pyridyl)-1H,3H-pyrrolo[1,2-c]thiazole-7-carboxylic acid and of 4.9 g of 1,1'-carbonyldiimidazole in 100 cm³ of tetrahydrofuran is stirred for 20 hours at approximately 20° C. The reaction mixture is then concentrated to dryness at reduced pressure (2.7 kPa) at a temperature close to 40° C., and the residue is taken up in 100 cm³ of water. The solid formed is drained on a glass sinter and washed with water and then recrystallized from 60 cm³ of acetonitrile. In this way 4.38 g of 7-(imidazolylcarbonyl)-6-methyl-5-(3-pyridyl)-1H,3H-pyrrolo[1,2-c]thiazole are obtained in the form of beige crystals which melt at 172° C.

Example 38

A suspension of 5.0 g of 6-methyl-5-(3-pyridyl)-1H,3H-pyrrolo[1,2-c]thiazole-7-carbonitrile and of 4.1 g of potassium hydroxide pellets in 40 cm³ of ethylene glycol is heated to reflux for 16 hours. The mixture is then concentrated at reduced pressure (14 Pa) at a temperature close to 80° C., to give a solid residue. The solid is taken up in 40 cm³ of water and acidified to pH=4 with 4 cm³ of hydrochloric acid (12N). The resulting precipitate is filtered off, washed with water and dried (4.3 g). A portion of the solid (1.24 g) thus obtained is recrystallized from 125 cm³ of acetonitrile to give 0.49 g of 6-methyl-5-(3-pyridyl)-1H,3H-pyrrolo[1,2-c]thiazole-7-carboxylic acid in the form of cream-coloured crystals which melt at 235° C. (decomposition).

6-Methyl-5-(3-pyridyl)-1H,3H-pyrrolo[1,2-c]thiazole-7-carbonitrile is described in European Patent Application EP 0147317.

Example 39

To a solution of 2.8 g of 2,7-dichloro-3-(2-chloro-3-pyridyl)-5,6-dihydroindolizine-1-carboxamide in 300 cm³ of ethanol, 500 mg of 10% palladium on charcoal are then added in 10 cm³ of ethanol. The mixture is then purged with argon and hydrogen is allowed to bubble through for 6 hours. The mixture is then purged with argon for 2 hours and then filtered on a No. 4 glass sinter. The filtrate is concentrated to dryness at reduced pressure (2.7 kPa). The residue is taken up with 300 cm³ of water (pH~2) and then the mixture is alkalified with a saturated solution of sodium hydrogencarbonate (pH~8). The white precipitate obtained is filtered off on a No. 4 glass sinter and washed with 2×20 cm of water. 2.19 g of a white solid are obtained, which is recrystallized from 20 cm³ of isopropanol. 1.91 g of 2-chloro-3-(2-chloro-3-pyridyl)-5,6,7,8-tetrahydroindolizine-1-carboxamide are thus obtained in the form of a white solid melting at 179° C.

2,7-Dichloro-3-(2-chloro-3-pyridyl)-5,6-dihydroindolizine-1-carboxamide is prepared as follows:

A mixture of 4.1 g of 3-(2-chloro-3-pyridyl)-5,6,7,8-tetrahydroindolizine-1-carboxamide and 6.3 g of N-chlorosuccinimide in 1 litre of acetonitrile is stirred in refluxing acetonitrile for 2 hours. The reaction mixture is concentrated to dryness at reduced pressure (2.7 kPa). 200 cm³ of a saturated solution of sodium hydrogencarbonate are added. The precipitate is filtered off on a No. 4 glass sinter, washed with 2×50 cm of water and dried. The solid obtained is chromatographed on a column of 8.5 cm diameter containing 1.7 kg of silica (0.02–0.04). Elution is carried out with a 95/5 by volume mixture of dichloromethane and of methanol at a total pressure of 1.5 bar and with 80-cm³ fractions being collected. The homogeneous fractions are combined and concentrated at reduced pressure (2.7 kPa) at a temperature close to 40° C., to give 1.4 g of a solid, which is recrystallized from 80 cm³ of acetonitrile. 0.84 g of 2,7-dichloro-3-(2-chloro-3-pyridyl)-5,6-dihydroindolizine-1-carboxamide are thus obtained in the form of a white solid melting at 262° C.

3-(2-Chloro-3-pyridyl)-5,6,7,8-tetrahydroindolizine-1-carboxamide is described in Example 4.

Example 40

2-Chloro-3-(2-fluoro-3-pyridyl)-5,6,7,8-tetrahydroindolizine-1-carboxamide is prepared according to the method described in Example 10, from 1.8 g of 2-chloro-3-(2-fluoro-3-pyridyl)-5,6,7,8- tetrahydroindolizine-1-carbonitrile and 30 cm³ of 60% sulphuric acid. 1.3 g of 2-chloro-3-(2-fluoro-3-pyridyl)-5,6,7,8-tetrahydroindolizine-1-carboxamide is thus obtained in the form of a white powder melting at 191° C.

2-Chloro-3-(2-fluoro-3-pyridyl)-5,6,7,8-tetrahydroindolizine-1-carbonitrile is prepared according to the method described in Example 39, from 3 g of a mixture of products containing approximately 60 mol % of 2-chloro-3-(2-fluoro-3-pyridyl)-5,6,7,8-tetrahydroindolizine-1-carbonitrile, 20% of 2,7-dichloro-3-(2-fluoro-3-pyridyl)-5,6-dihydroindolizine-1-carbonitrile and 10% of 2-chloro-3-(2-fluoro-3-pyridyl)-5,6-dihydroindolizine-1-carbonitrile and 0.6 g of 10% palladium on charcoal. 1.86 g of 2-chloro-3-(2-fluoro-3-pyridyl)-5,6,7,8-tetrahydroindolizine-1-carbonitrile are thus obtained in the form of a white powder melting at 134° C.

The mixture of products containing 60 mol % of 2-chloro-3-(2-fluoro-3-pyridyl)-5,6,7,8-tetrahydroindolizine-1-carbonitrile, 20% of 2,7-dichloro-3-(2-fluoro-3-pyridyl)-5,6-dihydroindolizine-1-carbonitrile and 10% of 2-chloro-3-(2-fluoro-3-pyridyl)-5,6-dihydroindolizine-1-carbonitrile is prepared according to the method described in Example 39 from 3 g of 3-(2-fluoro-3-pyridyl)-5,6,7,8-tetrahydroindolizine-1-carbonitrile and 2.48 g of N-chlorosuccinimide. 3 g of a mixture containing 60 mol % of 2-chloro-3-(2-fluoro-3-pyridyl)-5,6,7,8-tetrahydroindolizine-1-carbonitrile, 20% of 2,7-dichloro-3-(2-fluoro-3-pyridyl)-5,6-dihydroindolizine-1-carbonitrile and 10% of 2-chloro-3-(2-fluoro-3-pyridyl)-5,6-dihydroindolizine-1-carbonitrile are thus obtained.

3-(2-Fluoro-3-pyridyl)-5,6,7,8-tetrahydroindolizine-1-carbonitrile is prepared as in Example 5.

Example 41

2-Bromo-3-(2-chloro-3-pyridyl)-5,6,7,8-tetrahydroindolizine-1-carboxamide is prepared according to the method described in Example 2, from 2.29 g of 2-bromo-3-(2-chloro-3-pyridyl)-5,6,7,8-tetrahydroindolizine-1-carbonitrile and 45 cm³ of 12N hydrochloric acid (d=1.19). 0.55 g of a mixture containing 50 mol % of 2-chloro-3-(2-chloro-3-pyridyl)-5,6,7,8-tetrahydroindolizine-1-carboxamide and 50% of 2-bromo-3-(2-chloro-3-pyridyl)-5,6,7,8-tetrahydroindolizine-1-carboxamide are obtained. The mixture is separated by chromatography in subcritical phase on a 5-μm Kromasil column with $CO_2$ at 150 bars at 35° C. 158 mg of 2-bromo-3-(2-chloro-3-pyridyl)-5,6,7,8-tetrahydroindolizine-1-carboxamide are thus obtained in the form of a white solid with Rf=0.21 (thin layer chromatography on silica gel; ethyl acetate eluent).

2-Bromo-3-(2-chloro-3-pyridyl)-5,6,7,8-tetrahydroindolizine-1-carbonitrile is prepared as in Example 9.

Example 42

3-(5-Thiazolyl)-5,6,7,8-tetrahydroindolizine-7-carboxamide is prepared as described in Example 1, from 0.5 g of 3-(5-thiazolyl)-5,6,7,8-tetrahydroindolizine-7-carbonitrile and 10 cm³ of hydrochloric acid. 0.216 g of a beige powder melting at 174° C. are thus obtained.

3-(5-Thiazolyl)-5,6,7,8-tetrahydroindolizine-7-carbonitrile is prepared as described in Example 1, from 5.1 g of N-(5-thiazolylcarbonyl)-2-pipecolinic acid and from 3.67 g of 2-chloroacrylonitrile. 0.6 g of 3-(5-thiazolyl)-5,6,7,8-tetrahydroindolizine-7-carbonitrile are thus obtained in the form of an oil. (Rf=0.76; thin layer chromatography on silica gel; eluent: 95/5 dichloromethane/methanol).

N-(5-Thiazolylcarbonyl)-2-pipecolinic acid is prepared according to the following method:

7.7 g of ethyl N-(5-thiazolylcarbonyl)pipecolinate are added to a solution of 1.15 g of sodium hydroxide pellets in 150 cm³ of acetonitrile, 2 cm³ of water and 2 cm3 of ethanol. The mixture is stirred at ambient temperature for 16 hours. The mixture is evaporated at reduced pressure (2.7 kPa). The residue is taken up with 50 cm³ of ethyl acetate and 40 cm³ of water. The aqueous phase is then acidified with 27 cm³ of 1N hydrochloric acid and extracted with 2×200 cm³ of ethyl acetate. The organic phase is concentrated at reduced pressure (2.7 kPa). 5.31 g of N-(S-thiazolylcarbonyl)piperidine-2-carboxylic acid are thus obtained in the form of oil (Rf=0.9; thin layer chromatography on silica gel; eluent: 12/6/1 chloroform/methanol/aqueous ammonia).

Ethyl N-(5-thiazolylcarbonyl)pipecolinate is prepared as in Example 1, from 4.4 g of ethyl pipecolinate and 5.25 g of 5-chloroformylthiazole. 7.7 g of ethyl N8(5-thiazolylcarbonyl)pipecolinate are thus obtained in the form of brown oil. (Rf=0.51; thin layer chromatography on silica gel; eluent: 55/45 dichloromethane/ethyl acetate).

5-Chloroformylthiazole is prepared from 5 g of 5-thiazolecarboxylic acid in 80 cm3 [lacuna] 1,2-dichloroethane. The mixture is refluxed and 34.2 g of thionyl chloride are added dropwise. Refluxing is maintained for 2 hours 30 minutes after the addition and for 10 hours at ambient temperature. The mixture is concentrated at reduced pressure (2.7 kPa). 5.25 g of 5-chloroformylthiazole are thus obtained and employed crude.

5-Thiazolecarboxylic acid is prepared according to Erlenmeyer, von Meyenburg, Helvetica Acta, 29, 204 (1937).

Example 43

N-Chlorosuccinimide is added in 0.05 g portions to a solution of 0.1 g of 3-(5-thiazolyl)-5,6,7,8-tetrahydroindolizine-1-carboxamide in 10 cm³ of acetonitrile at 65° C. After 2 hours a precipitate is seen to form. The mixture is allowed to cool to approximately 20° C., the solid is filtered off and washed with two times 0.5 cm³ of acetonitrile. The operation was repeated another two times on 0.1 g of 3-(4-thiazolyl)-5,6,7,8-tetrahydroindolizine-1-carboxamide. The solids obtained in the three tests were combined and chromatographed on a column of 1.8 cm diameter containing 40 g of silica (0.063–0.220). Elution is carried out with a 95/5 mixture of dichloromethane and methanol, 2-cm3 fractions being collected. The homogeneous fractions are combined and concentrated at reduced pressure (2.7 kPa) at a temperature close to 40° C., to give a white solid which is taken up in ethyl ether and then filtered off and dried in air. 0.12 g of 2-chloro-3-(5-thiazolyl)-5,6,7,8-tetrahydroindolizine-1-carboxamide are thus obtained in the form of a white solid which melts at 227° C.

3-(5-Thiazolyl)-5,6,7,8-tetrahydroindolizine-1-carboxamide is prepared as in Example 42.

Example 44

2-Methyl-3-(3-pyridyl)-5,6,7,8-tetrahydroindolizine-1-carboxylic acid is prepared according to the following method:

1.46 g of potassium hydroxide pellets in 20 cm³ of water are added to a solution of 1.2 g of methyl 2-methyl-3-(3- pyridyl)-5,6,7,8-tetrahydroindolizine-1-carboxylate in 20 cm³ of ethanol. The mixture is heated to reflux for 20 hours. The mixture is then concentrated at reduced pressure (2.7 kPa). The oily residue is taken up with 100 cm³ of water and washed with 4×20 cm³ of dichloromethane. The aqueous phase is filtered and then cooled and acidified with a 1N aqueous solution of hydrochloric acid to pH~3–4. The solid is filtered off on a No. 4 glass sinter and washed with 4×30 cm³ of water. The solid obtained is recrystallized from 95 cm³ of a 60/40 ethanol/water mixture. 0.71 g of 2-methyl-3-(3-pyridyl)-5,6,7,8-tetrahydroindolizine-1-carboxylic acid are thus obtained in the form of a white powder melting at 250° C.

Methyl 2-methyl-3-(3-pyridyl)-5,6,7,8-tetrahydroindolizine-1-carboxylate is prepared as in Example 1, from 2.56 g of the sodium salt of N-nicotinoylpiperidine-2-carboxylic acid and 7.16 g of 2-bromo-2-methylbutenoate. 1.2 g of methyl 2-methyl-3-(3-pyridyl)-5,6,7,8-tetrahydroindolizine-1-carboxylate are thus obtained in the form of an orange oil (Rf=0.25; thin layer chromatography on silica gel; eluent: 8/2 dichloromethane/ethyl acetate).

The sodium salt of N-nicotinoylpiperidine-2-carboxylic acid is prepared as in Example 1, from 89 g of ethyl N-nicotinoylpiperidine-2-carboxylate and 45 g of sodium hydroxide. 16.2 g of the sodium salt of N-nicotinoylpiperidine-2-carboxylic acid are thus obtained in the form of a cream powder (Rf=0.49; thin layer chromatography on silica gel; eluent: 12/6/1 chloroform/methanol/aqueous ammonia).

Ethyl N-nicotinoylpiperidine-2-carboxylate is prepared by the method described in European Patent Application 118321.

Example 45

0.36 g of N-bromosuccinimide are added with stirring to a suspension of 0.51 g of methyl 3-(3-pyridyl)-5,6,7,8-tetrahydroindolizine-1-carboxylate in 10 cm³ of ethyl acetate. The mixture is left stirred for 5 days. The reaction mixture is filtered and the solution is concentrated at reduced pressure (2.7 kPa) at a temperature close to 40° C. The residue is taken up with 10 cm³ of water. The precipitate thus formed is filtered off, washed with water and then dried in air. 0.58 g of the expected product are thus obtained in the form of beige powder melting at 140° C.

Methyl 3-(3-pyridyl)-5,6,7,8-tetrahydroindolizine-1-carboxylate can be prepared as follows:

1.33 g of methyl propionate are added to a solution of 3.01 g of para-toluenesulphonyl chloride in 17 cm3 of dichloromethane. A solution of the triethylamine salt of N-nicotinoylpiperidine-2-carboxylic acid in 17 cm³ of dichloromethane, prepared from 3.38 g of N-nicotinoylpiperidine-2-carboxylic acid and 2 cm³ of triethylamine, is added slowly with stirring. 2.3 cm³ of triethylamine are then added slowly. The mixture is kept at 25° C. with stirring overnight at ambient temperature. The reaction mixture is concentrated at reduced pressure (2.7 kPa) at a temperature close to 40° C. A residue is thus obtained, which is taken up in 25 cm³ of ethyl acetate and filtered. The filtrate is concentrated at reduced pressure (2.7 kPa) at a temperature close to 40° C. This residue is taken up again in 25 cm³ of ethyl acetate and filtered and then the filtrate is concentrated to dryness. The residue is crystallized from 15 cm³ of ethyl ether. The solid is filtered off and dried in air. 1.1 g of methyl 3-(3-pyridyl)-5,6,7,8-tetrahydroindolizine-1-carboxylate are thus obtained in the form of a cream solid melting at 122° C., containing approximately 5% of methyl 3-(3-pyridyl)-5,6,7,8-tetrahydroindolizine-2-carboxylate.

N-Nicotinoylpiperidine-2-carboxylic acid is prepared as described in European Patent Application 118321.

Example 46

2-Chloro-3-(3-pyridyl)-5,6,7,8-tetrahydroindolizine-1-carboxylic acid is prepared as in Example 44, from 0.9 g of methyl 2-chloro-3-(3-pyridyl)-5,6,7,8-tetrahydroindolizine-1-carboxylate. 0.72 g of 2-chloro-3-(3-pyridyl)-5,6,7,8-tetrahydroindolizine-1-carboxylic acid are thus obtained in the form of a white powder (Rf=0.43; thin layer chromatography on silica gel; eluent: 9/1 dichloromethane/methanol).

Methyl 2-chloro-3-(3-pyridyl)-5,6,7,8-tetrahydroindolizine-1-carboxylate is prepared as in Example 39, from 1.4 g of methyl 2,7-dichloro-3-(3-pyridyl)-5,6-dihydroindolizinecarboxylate and 0.28 g of 10% palladium on charcoal. 0.9 g of methyl 2-chloro-3-(3-pyridyl)-5,6,7,8-tetrahydroindolizine-1-carboxylate are thus obtained in the form of beige powder melting at 111° C.

Methyl 2,7-dichloro-3-(3-pyridyl)-5,6-dihydroindolizinecarboxylate is prepared as in Example 39, from 1 g of methyl 3-(3-pyridyl)-5,6,7,8-tetrahydroindolizine-1-carboxylate and 1.56 g of N-chlorosuccinimide. 0.7 g of methyl 2,7-dichloro-3-(3-pyridyl)-5,6-dihydroindolizine-1-carboxylate are thus obtained in the form of an orange oil (Rf=0.33; thin layer chromatography on silica gel; eluent: 8/2 dichloromethane/ethyl acetate).

Methyl 3-(3-pyridyl)-5,6,7,8-tetrahydroindolizine-1-carboxylate is prepared as in Example 45.

Example 47

1 cm³ of 5N sodium hydroxide is added with stirring to a solution of 0.34 g of methyl 2-bromo-3-(3-pyridyl)-5,6,7,8-tetrahydroindolizine-1-carboxylate in methanol at 20° C. The orangy solution is heated to reflux for 15 hours. The solvent is then evaporated off at reduced pressure (2.7 kPa) at a temperature close to 40° C. The residue is taken up with 10 cm³ of water and acidified to pH~3 with 0.2 cm³ of 12N hydrochloric acid and 0.5 cm³ of 1N acetic acid. The precipitate is filtered off, washed with water and then dried in air. 0.29 g of 2-bromo-3-(3-pyridyl)-5,6,7,8-tetrahydroindolizine-1-carboxylic acid are thus obtained in the form of a cream powder which melts at >260° C., with decomposition.

Example 48

2-Chloro-3-(N-oxide-3-pyridyl)-5,6,7,8-tetrahydroindolizine-1-carboxamide is prepared according to the following method:

3.8 g of meta-chloroperoxybenzoic acid are added to a suspension of 1.5 g of 2-chloro-3-(3-pyridyl)-5,6,7,8-tetrahydroindolizine-1-carboxamide. The mixture is kept stirred at ambient temperature for 5 hours and then washed with 2×100 cm³ of a saturated solution of sodium hydrogencarbonate. The organic phase is dried over magnesium sulphate and concentrated at reduced pressure (2.7 kPa). The residue is chromatographed on a column of 4 cm diameter containing 450 g of silica (0.04–0.02). Elution is carried out with a 95/5 mixture of dichloromethane/methanol, 25-cm³ fractions being collected. The homogeneous fractions are combined and concentrated at reduced pressure (2.7 kPa).

1.07 g of a solid are thus obtained, which is recrystallized once from 20 cm³ of isopropyl ether and then from 80 cm³ of ethanol. 0.74 g of 2-chloro-3-(N-oxide-3-pyridyl)-5,6,7,8-tetrahydroindolizine-1-carboxamide are thus obtained in the form of a white powder (Rf=0.24; thin layer chromatography on silica gel; eluent: 90/10 dichloromethane/methanol).

Example 49

6-Chloro-5-(3-pyridyl)-2,3-dihydropyrolizine-7-carboxamide is prepared as described in Example 45, from 0.45 g of 5-(3-pyridyl)-2,3-dihydropyrrolizine-7-carboxamide and 0.29 g of N-chlorosuccinimide. 0.27 g of expected product are thus obtained in the form of cream powder which melts at 215° C.

5-(3-Pyridyl)-2,3-dihydropyrrolizine-7-carboxylic acid can be prepared in the following manner:

A suspension of 2.5 g of 5-(3-pyridyl)-2,3-dihydropyrrolizine-7-carbonitrile and of 3.4 g of potassium hydroxide pellets in 25 cm³ of tert-butanol is heated to reflux for 2 hours. The mixture is then cooled to approximately 25° C. and diluted with 50 cm³ of water; a slow crystallization is then noted: After 15 hours the crystals are filtered off, washed with water and dried in air. 1.14 g of 5-(3-pyridyl-2,3-dihydropyrrolizine-7-carboxylic acid are thus obtained in the form of a white solid which melts at 210° C.

5-(3-Pyridyl)-2,3-dihydropyrrolizine-7-carbonitrile is prepared by the method described in Example 45, from 5.0 g of N-nicotinylproline and 2.19 g of 2-chloroacrylonitrile. 2.6 g of expected product are thus obtained in the form of a beige solid melting at about 136° C.

Example 50

1-Acetyl-3-(3-pyridyl)-5,6,7,8-tetrahydroindolizine is prepared according to the following method:

9.3 cm³ of acetic acid are added dropwise to a solution of 8.1 g of methyl 2-(methoxycarbonyl)-3-oxo-3-[3-(3-pyridyl)-5,6,7,8-tetrahydro-1-indolizinyl]propionate in 20 cm³ of distilled water, followed by 1.2 cm³ of concentrated sulphuric acid. The mixture is then heated to reflux for 20 hours and is then cooled to ambient temperature, diluted with 60 cm³ of distilled water and filtered on paper. The filtrate is cooled in an ice bath and treated dropwise with 27.5 cm³ of 10N sodium hydroxide to pH 11. The resulting two-phase mixture is extracted 4 times with 100 cm³ of ethyl acetate. The organic extracts are combined and washed with 70 cm³ of distilled water and are then dried over magnesium sulphate and concentrated at reduced pressure (2.7 kPa). The solid obtained is chromatographed on a column containing 200 g of silica (0.02–0.05). Elution is carried out with a 50/50 by volume mixture of ethyl acetate and of cyclohexane at a total pressure of 1.4 bar and with 40-cm³ fractions being collected. The homogeneous fractions are combined and concentrated at reduced pressure (2.7 kPa) to give 3.3 g of a white solid, which is recrystallized from 20 cm³ of isopropyl ether and 3 cm³ of ethanol. 2.1 g of 1-acetyl-3-(3-pyridyl)-5,6,7,8-tetrahydroindolizine are thus obtained in the form of white crystals melting at 109° C.

Methyl 2-(methoxycarbonyl)-3-oxo-3-[3-(3-pyridyl)-5,6,7,8-tetrahydro-1-indolizinyl]propionate is prepared according to the following method:

6.8 cm³ of triethylamine are added dropwise to a suspension of 1.4 g of magnesium chloride in 16 cm³ of acetonitrile under argon, followed, after 5 minutes, by 2.9 cm³ of dimethyl malonate. The resulting white suspension is then stirred at ambient temperature under argon for 1 hour. To this suspension is then added, via a cannula, a suspension, prepared beforehand from 6.3 g of the chloride of 3-(3-pyridyl)-5,6,7,8-tetrahydroindolizine-1-carboxylic acid in 36 cm³ of acetonitrile under argon, to which 2.8 cm³ of triethylamine has been added. The resulting brick-red suspension is stirred at ambient temperature under argon for 18 hours and is then cooled to 0° C. and treated dropwise with 7 cm³ of concentrated hydrochloric acid. The resulting mixture is diluted with 15 cm³ of distilled water and separated and then the aqueous phase is extracted 6 times with 50 cm³ of dichloromethane. The organic extracts are combined and dried over magnesium sulphate and then concentrated at reduced pressure (2.7 kPa). 8.1 g of methyl 2-(methoxycarbonyl)-3-oxo-3-[3-(3-pyridyl)-5,6,7,8-tetrahydro-1-indolizinyl]propionate are thus obtained in the form of a beige crystalline solid melting at 146–150° C. (Rf=0.65; thin layer chromatography on silica gel; eluent: 10/90 by volume mixture of methanol and of dichloromethane).

The chloride of 3-(3-pyridyl)-5,6,7,8-tetrahydroindolizine-1-carboxylic acid is prepared according to the following method:

4.3 cm³ of thionyl chloride are added dropwise to a suspension 4.8 g of 3-(3-pyridyl)-5,6,7,8-tetrahydroindolizine-1-carboxylic acid in 120 cm³ of chloroform, followed by a few drops of dimethylformamide. The resulting suspension is then stirred at ambient temperature for 16 hours (slow gas release) and is then heated to reflux (75° C.) for 1 hour, at the end of which there is no further gas release. It is then cooled to ambient temperature and then concentrated at reduced pressure (2.7 kPa) and taken up twice in ethanol-free dichloromethane and then concentrated again in the same way. 5.4 g of 3-(3-pyridyl-5,6,7,8-tetrahydroindolizine-1-carboxylic acid are thus obtained in the form of a greenish solid. (Rf=0.44; thin layer chromatography on silica gel; eluent: 10/90 by volume mixture of methanol and of dichloromethane).

3-(3-Pyridyl)-5,6,7,8-tetrahydroindolizine-1-carboxylic acid is described in European Patent Application 147317.

Example 51

1-Acetyl-2-bromo-3-(3-pyridyl)-5,6,7,8-tetrahydroindolizine is prepared as described in Example 23, from 1.2 g of 1-acetyl-3-(3-pyridyl)-5,6,7,8-tetrahydroindolizine and 1.1 g of N-bromosuccinimide. 0.6 g of 1-acetyl-2-bromo-3-(3-pyridyl)-5,6,7,8-tetrahydroindolizine are thus obtained in the form of white crystals melting at 163° C.

Example 52

1-Acetyl-2-chloro-3-(3-pyridyl)-5,6,7,8-tetrahydroindolizine is prepared as described in Example 39, from 1.7 g of 1-acetyl-2,7-dichloro-3-(3-pyridyl)-5,6-dihydroindolizine and from 0.09 g of 10% palladium on charcoal. 0.05 g of 1-acetyl-2-chloro-3-(3-pyridyl)-5,6,7,8-tetrahydroindolizine are thus obtained in the form of whitish crystalline solid melting at 115° C.

1-Acetyl-2,7-dichloro-3-(3-pyridyl)-5,6-dihydroindolizine is prepared as described in Example 39, from 1.2 g of 1-acetyl-3-(3-pyridyl)-5,6,7,8-tetrahydroindolizine and 2.2 g of N-chlorosuccinimide. 1.7 g of 1-acetyl-2,7-dichloro-3-(3-pyridyl)-5,6-dihydroindolizine are thus obtained in the form of yellow crystalline solid. (Rf=0.25; thin layer chromatography on silica gel; eluent: 5/95 by volume mixture of methanol and of dichloromethane).

Example 53

2-Methoxy-3-(3-pyridyl)-5,6,7,8-tetrahydroindolizine-1-carboxamide is prepared as described in Example 24, from 1.4 g of 2-methoxy-3-(3-pyridyl-5,6,7,8-tetrahydroindolizine-1-carbonitrile and of 1.6 g of potassium hydroxide. 1.1 g of 2-methoxy-3-(3-pyridyl)-5,6,7,8-tetrahydroindolizine-1-carboxamide are thus obtained in the form of yellowish crystals melting at 186° C.

2-Methoxy-3-(3-pyridyl)-5,6,7,8-tetrahydroindolizine-1-carbonitrile is prepared as described in Example 1, from 8.0 g of N-nicotinoylpiperidine-2-carboxylic acid and from 31.6 g of 2-bromo-3-methoxyacrylonitrile. 1.4 g of 2-methoxy-3-(3-pyridyl)-5,6,7,8-tetrahydroindolizine-1-carbonitrile are thus obtained in the form of a whitish crystalline solid melting at 159° C.

N-Nicotinoylpiperidine-2-carboxylic acid is prepared according to European Patent Application 118321.

2-Bromo-3-methoxyacrylonitrile is described in Japanese Patent 116650.

Example 54

2-Cyano-3-(3-pyridyl)-5,6,7,8-tetrahydroindolizine-1-carboxamide is prepared according to the same method described in Example 11, from 2.12 g of 2-cyano-3-(3-pyridyl)-5,6,7,8-tetrahydroindolizine-1-carbonitrile and 1.69 g of an aqueous solution of potassium hydroxide. 0.72 g of 2-cyano-3-(3-pyridyl)-5,6,7,8-tetrahydroindolizine-1-carboxamide are thus obtained in the form of a white solid melting at 244° C.

2-Cyano-3-(3-pyridyl)-5,6,7,8-tetrahydroindolizine-1-carbonitrile is prepared according to the same method described in Example 15, from 19.3 g of a mixture of approximately 35 mol % of 3-(3-pyridyl)-5,6,7,8-tetrahydroindolizine-1-carbonitrile and 65 mol % of 3-(3-pyridyl)-5,6,7,8-tetrahydroindolizine-2-carbonitrile and from 36.6 g of sulphonyl isocyanate chloride. 2.8 g of 2-cyano-3-(3-pyridyl)-5,6,7,8-tetrahydroindolizine-1-carbonitrile are thus obtained in the form of a white solid melting at 178° C.

The mixture of approximately 35 mol % of 3-(3-pyridyl)-5,6,7,8-tetrahydroindolizine-1-carbonitrile and 65 mol % of 3-(3-pyridyl)-5,6,7,8-tetrahydroindolizine-2-carbonitrile is described in European Patent Application 124384.

Example 55

25 $cm^3$ of acetic acid are added to a solution of 3 g of 2,7-dichloro-3-(2-methyl-3-pyridyl)-5,6-dihydroindolizine-1-carboxamide in 250 $cm^3$ of ethanol. 500 mg of 10% palladium on charcoal are then added in 10 $cm^3$ of ethanol. The mixture is purged with argon and hydrogen is allowed to bubble through for 1 hour 30 min. The mixture is then purged with argon for 2 hours and then filtered on a No. 4 glass sinter. The filtrate is concentrated to dryness at reduced pressure (2.7 kPa). The residue is taken up with 300 $cm^3$ of water (pH~4) and then the mixture is alkalified with a saturated solution of sodim hydrogencarbonate (pH~8). The white precipitate obtained is filtered on a No. 4 glass sinter and washed with 2×20 $cm^3$ of water. 2.69 g of a white solid are obtained, which is filtered on a column of 3.6 cm diameter containing 45 g of silica (0.02–0.04). Elution is carried out with a 90/10 dichloromethane/methanol mixture, 10-$cm^3$ fractions being collected. Fractions from 7 to 16 are combined and concentrated at reduced pressure (2.7 kPa). 2.37 g of a pale yellow solid are obtained, and this is recrystallized from 40 $cm^3$ of isopropanol. 0.945 g of 2-chloro-3-(2-methyl-3-pyridyl)-5,6,7,8-tetrahydroindolizine-1-carboxamide are thus obtained in the form of a white solid melting at 195° C.

10 2,7-Dichloro-3-(2-methyl-3-pyridyl)-5,6-dihydroindolizine-1-carboxamide is prepared as follows:

A mixture of 21.85 g [lacuna] 3-(2-methyl-3-pyridyl)-5,6,7,8-tetrahydroindolizine-1-carboxamide and 34.24 g of N-chlorosuccinimide in 1.5 liters of acetonitrile is stirred in refluxing acetonitrile for 2 hours. The reaction mixture is concentrated to dryness at reduced pressure (2.7 kPa). 200 $cm^3$ of a saturated solution of sodium hydrogencarbonate are added. The precipitate is filtered on a No. 4 glass sinter, washed with 2×50 $cm^3$ of water and dried. The solid obtained is chromatographed on a column of 8.5 cm diameter containing 1.7 kg of silica (0.02–0.04). Elution is carried out with a 95/5 by volume mixture of dichloromethane and of methanol at a total pressure of 1.5 bar and with 100-$cm^3$ fractions being collected. The homogeneous fractions are combined and concentrated at reduced pressure (2.7 kPa) at a temperature close to 40° C., to give 5.6 g of a brown solid, which is recrystallized from 250 $cm^3$ of acetonitrile. 5.42 g of 2,7-dichloro-3-(2-methyl-3-pyridyl)-5,6-dihydroindolizine-1-carboxamide are thus obtained in the form of a white solid melting at 223° C.

3-(2-Methyl-3-pyridyl)-5,6,7,8-tetrahydroindolizine-1-carboxamide is prepared as described in Example 11, from 23.3 g of 3-(2-methyl-3-pyridyl)-5,6,7,8-tetrahydroindolizine-1-carbonitrile and 33 g of potassium hydroxide. 21.85 g of 3-(2-methyl-3-pyridyl)-5,6,7,8-tetrahydroindolizine-1-carboxamide are thus obtained in the form of a white solid melting at 244° C.

3-(2-Methyl-3-pyridyl)-5,6,7,8-tetrahydroindolizine-1-carbonitrile is prepared as in Example 1, from 39.66 g of the sodium salt of N-(2-methylnicotinoyl)piperidine-2-carboxylic acid and 14.1 g of 2-chloroacrylonitrile. 19.38 g of 3-(2-methyl-3-pyridyl)-5,6,7,8-tetrahydroindolizine-1-carbonitrile are thus obtained in the form of a white solid melting at 154° C.

The sodium salt of N-(2-methylnicotinoyl)piperidine-2-carboxylic acid is prepared as in Example 1, from 56.24 g of ethyl N-(2-methylnicotinoyl)piperidine-2-carboxylate and 8 g of sodium hydroxide. 39.66 g of the sodium salt of N-(2-methylnicotinoyl)piperidine-2-carboxylic acid are thus obtained in the form of a white solid melting at 150° C.

Ethyl N-(2-methylnicotinoyl)piperidine-2-carboxylate is prepared according to the following method:

150.8 g of 1-(3-dimethylaminopropyl)-3-ethylcarbodiimide hydrochloride and 60.3 g of 1-hydroxybenzotriazole hydrate are added to a suspension of 82.4 g of ethyl piperidine-2-carboxylate in 500 $cm^3$ of dichloromethane. The solution remains milky and 45 g of 2-methylnicotinic acid are added. The solution becomes clear and 161 $cm^3$ of triethylamine are added. The mixture is kept stirred at ambient temperature overnight. The mixture is hydrolysed with 2×1 liter of water. The organic phase is then dried over magnesium sulphate and evaporated at reduced pressure (2.7 kPa). The oil obtained is chromatographed on a column of 8 cm diameter containing 900 g of silica (0.04–0.02). Elution is carried out with ethyl acetate, 70-$cm^3$ fractions being collected. The homogeneous fractions are combined and concentrated at reduced pressure (2.7 kPa). 81.86 g of ethyl N-(2-methylnicotinoyl)piperidine-2-carboxylate are thus obtained in the form of a colourless oil (Rf=0.21; thin layer chromatography on silica gel; ethyl acetate eluent).

Example 56

The following products are prepared by operating as in the above examples:
2-fluoro-3-(3-pyridyl)-5,6,7,8-tetrahydroindolizine-1-carboxamide;
2-fluoro-3-(2-chloro-3-pyridyl)-5,6,7,8-tetrahydroindolizine-1-carboxamide;
2-fluoro-3-(2-fluoro-3-pyridyl)-5,6,7,8-tetrahydroindolizine-1-carboxamide;
2-fluoro-3-(5-thiazolyl)-5,6,7,8-tetrahydroindolizine-1-carboxamide;
6-fluoro-5-(3-pyridyl)-2,3-dihydropyrrolizine-7-carboxamide;
2-fluoro-3-(3-pyridyl)-5,6,7,8-tetrahydroindolizine-1-acetyl.

What is claimed is:
1. A pyrrole derivative having the formula (I):

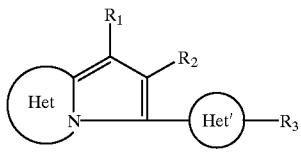

(I)

in which
Het denotes a ring condensed with pyrrole to form a 5,6,7,8-tetrahydroindolizine ring, Het' is a pyridyl or pyridyl N-oxide radical; $R_2$ is a hydrogen or halogen atom or an alkyl, alkenyl, trihalomethyl or cyano radical, $R_3$ is a hydrogen or halogen atom or a hydroxyl or alkyl radical, and $R_1$ is alkoxycarbonyl, acyl containing 1, 3 or 4 carbon atoms or imidazolyl carbonyl; or Het denotes a ring condensed with pyrrole to form a 5,6,7,8-tetrahydroindolizine ring, Het' is a pyridyl or pyridyl N-oxide radical, $R_1$ is a carboxamide, cyano, carboxyl, alkoxycarbonyl, acyl or imidazolylcarbonyl radical, $R_3$ is a hydrogen or halogen atom or a hydroxyl or alkyl radical, and $R_2$ is alkenyl, trihalomethyl or cyano; or Het denotes a ring condensed with pyrrole to form a 5,6,7,8-tetrahydroindolizine ring, $R_1$ is a carboxamide, cyano, carboxyl, alkoxycarbonyl, acyl or imidazolylcarbonyl radical, $R_2$ is a halogen atom or an alkyl, alkenyl, trihalomethyl or cyano radical, $R_3$ is a hydrogen or halogen atom or a hydroxyl or alkyl radical, and Het' is 4-pyridyl or 2-pyridyl; or Het denotes a ring condensed with pyrrole to form a 5,6,7,8-tetrahydroindolizine ring, $R_1$ is a carboxamide, cyano, carboxyl, alkoxycarbonyl, acyl or imidazolylcarbonyl radical, $R_2$ is a hydrogen or halogen atom or an alkyl, alkenyl, trihalomethyl or cyano radical, and $R_3$ is halogen or hydroxyl, and Het' is 3-pyridyl,
or a pharmaceutically acceptable salt thereof.

2. A pyrrole derivative, said pyrrole derivative being
2-bromo-3-(3-pyridyl)-5,6,7,8-tetrahydroindolizine-1-carbonitrile;
2-bromo-3-(3-pyridyl)-5,6,7,8-tetrahydroindolizine-1-carboxamide;
2-iodo-3-(3-pyridyl)-5,6,7,8-tetrahydroindolizine-1-carboxamide;
2-methyl-3-(3-pyridyl)-5,6,7,8-tetrahydroindolizine-1-carbonitrile;
2-methyl-3-(3-pyridyl)-5,6,7,8-tetrahydroindolizine-1-carboxamide;
2-ethyl-3-(3-pyridyl)-5, 6,7, 8-tetrahydroindolizine-1-carbonitrile;
2-chloro-3-(3-pyridyl)-5,6,7,8-tetrahydroindolizine-1-carboxamide;
2-methyl-3-(3-pyridyl)-5,6,7,8-tetrahydroindolizine-1-carboxylic acid;
2-chloro-3-(3-pyridyl)-5,6,7,8-tetrahydroindolizine-1-carboxylic acid;
2-bromo-3-(3-pyridyl)-5,6,7,8-tetrahydroindolizine-1-carboxylic acid;
1-acetyl-3-(3-pyridyl)-5,6,7,8-tetrahydroindolizine; or
1-acetyl-2-bromo-3-(3-pyridyl)-5,6,7,8-tetrahydroindolizine.

3. A pyrrole derivative according to claim 2, which is 2-bromo-3-(3-pyridyl)-5,6, 7,8-tetrahydroindolizine-1-carboxamide.

4. A pyrrole derivative according to claim 2, which is 2-chloro-3-(3-pyridyl)-5,6,7,8-tetrahydroindolizine-1-carboxamide.

5. A method for preparing 2-chloro-3-(3-pyridyl)-5,6,7,8-tetrahydroindolizine-1-carboxamide, said method comprising treating 3-(pyridin-3-yl)-5,6,7,8-tetrahydroindolizine-1-carbonitrile with N-chlorosuccinimide; hydrolyzing the product of said treatment into the corresponding carboxamide, wherein 2-chloro-3-(pyridin-3-yl)-5,6-dihydroindolizine-1-carboxamide is a by-product of said hydrolysis; and reducing said 2-chloro-3-(pyridin-3-yl)-5,6-dihydroindolizine-1-carboxamide by hydrogenation.

6. A pharmaceutical composition for the prevention or treatment of a disorder involving tumor necrosis factor, said composition comprising a pharmaceutically effective amount of at least one product derived from a pyrrole derivative as recited in claim 1, or a pharmaceutically acceptable salt thereof, in association with a pharmaceutically acceptable diluent or adjuvant.

7. A method for preventing or treating a disorder involving tumor necrosis factor, wherein the disorder is a retroviral infection, said method comprising administering to a host in need thereof an effective amount of a pyrrole derivative having the formula I:

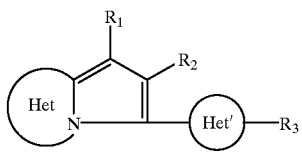

(I)

in which
Het denotes a ring condensed with pyrrole to form a 5,6,7,8-tetrahydroindolizine ring, Het' is a pyridyl or pyridyl N-oxide radical; $R_2$ is a hydrogen or halogen atom or an alkyl, alkenyl, trihalomethyl or cyano radical, $R_3$ is a hydrogen or halogen atom or a hydroxyl or alkyl radical, and $R_1$ is alkoxycarbonyl, acyl containing 1, 3 or 4 carbon atoms or imidazolyl carbonyl; or Het denotes a ring condensed with pyrrole to form a 5,6,7,8-tetrahydroindolizine ring, Het' is a pyridyl or pyridyl N-oxide radical, $R_1$ is a carboxamide, cyano, carboxyl, alkoxycarbonyl, acyl or imidazolylcarbonyl radical, $R_3$ is a hydrogen or halogen atom or a hydroxyl or alkyl radical, and $R_2$ is alkenyl, trihalomethyl or cyano; or Het denotes a ring condensed with pyrrole to form a 5,6,7,8-tetrahydroindolizine ring, $R_1$ is a carboxamide, cyano, carboxyl, alkoxycarbonyl, acyl or imidazolylcarbonyl radical, $R_2$ is a hydrogen or halogen atom or an alkyl, alkenyl, trihalomethyl or cyano radical, $R_3$ is a hydrogen or halogen atom or a hydroxyl or alkyl radical, and Het' is 4-pyridyl or 2-pyridyl; or Het denotes a ring condensed with pyrrole to form a 5,6,7,8-tetrahydroindolizine ring, $R_1$ is a carboxamide, cyano, carboxyl, alkoxycarbonyl, acyl or imidazolylcarbonyl radical, $R_2$ is a hydrogen or halogen atom or an alkyl, alkenyl, trihalomethyl or cyano radical, and $R_3$ is halogen or hydroxyl, and Het' is 3-pyridyl, or a pharmaceutically acceptable salt thereof.

8. A method according to claim 7, wherein said pyrrole derivative is 2-bromo-3-(3-pyridyl)-5,6,7,8-tetrahydroindolizine-1-carboxamide.

9. A method according to claim 7, wherein said pyrrole derivative is 2-chloro-3-(3-pyridyl)-5,6,7,8-tetrahydroindolizine-1-carboxamide.

10. A method according to claim 7, wherein said pyrrole derivative is 2-chloro-3-(2-chloro-3-pyridyl)-5,6,7,8-tetrahydro-indolizine-1-carboxamide.

11. A method according to claim 7, wherein said pyrrole derivative is 2-chloro-3-(2-fluoro-3-pyridyl)-5,6,7,8-tetrahydro-indolizine-1-carboxamide.

12. A method according to claim 7, wherein said pyrrole derivative is 2-cyano-3-(3-pyridyl)-5,6,7,8-tetrahydroindolizine-1-carboxamide.

13. A method according to claim 7, wherein said retroviral infection is AIDS or an AIDS related complex.

14. A method for preventing or treating a disorder involving tumor necrosis factor, wherein said prevention or treatment involves inhibiting the activation and/or production of the HIV virus, said method comprising administering to a host in need thereof an effective amount for said prevention or treatment of a pyrrole derivative having the formula I:

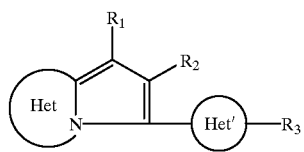

(I)

in which

Het denotes a ring condensed with pyrrole to form a 5,6,7,8-tetrahydroindolizine ring, Het' is a pyridyl or pyridyl N-oxide radical; $R_2$ is a hydrogen or halogen atom or an alkyl, alkenyl, trihalomethyl or cyano radical, $R_3$ is a hydrogen or halogen atom or a hydroxyl or alkyl radical, and $R_1$ is alkoxycarbonyl, acyl containing 1, 3 or 4 carbon atoms or imidazolyl carbonyl; or Het denotes a ring condensed with pyrrole to form a 5,6,7,8-tetrahydroindolizine ring, Het' is a pyridyl or pyridyl N-oxide radical, $R_1$ is a carboxamide, cyano, carboxyl, alkoxycarbonyl, acyl or imidazolylcarbonyl radical, $R_3$ is a hydrogen or halogen atom or a hydroxyl or alkyl radical, and $R_2$ is alkenyl, trihalomethyl or cyano; or Het denotes a ring condensed with pyrrole to form a 5,6,7,8-tetrahydroindolizine ring, R, is a carboxamide, cyano, carboxyl, alkoxycarbonyl, acyl or imidazolylcarbonyl radical, $R_2$ is a hydrogen or halogen atom or an alkyl, alkenyl, trihalomethyl or cyano radical, $R_3$ is a hydrogen or halogen atom or a hydroxyl or alkyl radical, and Het' is 4-pyridyl or 2-pyridyl; or Het denotes a ring condensed with pyrrole to form a 5,6,7,8-tetrahydroindolizine ring, $R_1$ is a carboxamide, cyano, carboxyl, alkoxycarbonyl, acyl or imidazolylcarbonyl radical, $R_2$ is a hydrogen or halogen atom or an alkyl, alkenyl, trihalomethyl or cyano radical, and $R_3$ is halogen or hydroxyl, and Het' is 3-pyridyl, or a pharmaceutically acceptable salt thereof.

* * * * *

UNITED STATES PATENT AND TRADEMARK OFFICE
CERTIFICATE OF CORRECTION

PATENT NO. : 6,194,426 B1
DATED : February 27, 2001
INVENTOR(S) : Eric Bacque et al.

It is certified that error appears in the above-identified patent and that said Letters Patent is hereby corrected as shown below:

<u>Title page,</u>
Item (73), "Assignee: Rhona-Poulenc Rorer S.A." should read -- Assignee: Rhone-Poulenc Rorer, S.A. --.

Signed and Sealed this

Twenty-first Day of August, 2001

*Attest:*

NICHOLAS P. GODICI
*Attesting Officer*    *Acting Director of the United States Patent and Trademark Office*